(12) United States Patent
Dierkes et al.

(10) Patent No.: US 11,676,422 B2
(45) Date of Patent: Jun. 13, 2023

(54) DEVICES, SYSTEMS AND METHODS FOR PREDICTING GAZE-RELATED PARAMETERS

(71) Applicant: PUPIL LABS GmbH, Berlin (DE)

(72) Inventors: Kai Dierkes, Berlin (DE); Moritz Kassner, Berlin (DE)

(73) Assignee: PUPIL LABS GmbH, Berlin (DE)

( * ) Notice: Subject to any disclaimer, the term of this patent is extended or adjusted under 35 U.S.C. 154(b) by 29 days.

(21) Appl. No.: 17/612,616

(22) PCT Filed: Jun. 5, 2019

(86) PCT No.: PCT/EP2019/064656
§ 371 (c)(1),
(2) Date: Nov. 19, 2021

(87) PCT Pub. No.: WO2020/244752
PCT Pub. Date: Dec. 10, 2020

(65) Prior Publication Data
US 2022/0206573 A1    Jun. 30, 2022

(51) Int. Cl.
*G06V 40/18* (2022.01)
*G06T 7/73* (2017.01)
(Continued)

(52) U.S. Cl.
CPC ....... *G06V 40/193* (2022.01); *G02B 27/0093* (2013.01); *G02B 27/0101* (2013.01);
(Continued)

(58) Field of Classification Search
CPC ............ G02B 27/0093; G02B 27/0172; G02B 2027/0138; G02B 2027/014;
(Continued)

(56) References Cited

U.S. PATENT DOCUMENTS

| 4,852,988 A | 8/1989 | Velez et al. |
| 6,091,546 A | 7/2000 | Spitzer |

(Continued)

FOREIGN PATENT DOCUMENTS

| CA | 2967756 | 10/2005 |
| CA | 2750287 | 11/2011 |

(Continued)

OTHER PUBLICATIONS

Swirski, Dodgson: "A fully-automatic, temporal approach to single camera, glint-free 3D eye model filling", Proc. PETMEI Lund/Sweden, Aug. 13, 2013.

(Continued)

*Primary Examiner* — Nelson M Rosario
(74) *Attorney, Agent, or Firm* — Dicke, Billig & Czaja, PLLC

(57) ABSTRACT

A system and method for generating data suitable for determining a parameter of a human eye. The method includes receiving a first image of the eye for a first time from a camera of known camera intrinsics defining an image plane, and determining a first ellipse in the first image. The method includes determining a first eye intersecting line expected to intersect a center of the eyeball at the first time as a line which is, in the direction of the orientation vector, parallel-shifted to the first center line by an expected distance between the center of the eyeball and a center of the pupil.

17 Claims, 6 Drawing Sheets

(51) Int. Cl.
*G02B 27/00* (2006.01)
*G02B 27/01* (2006.01)
*G06F 3/01* (2006.01)
*G06V 40/19* (2022.01)

(52) U.S. Cl.
CPC ........... *G02B 27/017* (2013.01); *G06F 3/013* (2013.01); *G06T 7/75* (2017.01); *G06V 40/19* (2022.01); *G06V 40/197* (2022.01); *G02B 2027/0138* (2013.01); *G02B 2027/0178* (2013.01)

(58) Field of Classification Search
CPC .... G02B 2027/0147; G02B 2027/0187; G02B 27/017; G06F 17/18; G06F 3/011; G06F 3/012; G06F 3/013; G06N 3/02; G06N 3/044; G06N 3/049; G06N 3/08; G06N 3/084; G06N 7/01; G06T 7/292; G06V 10/82; G06V 20/20; G06V 40/18
See application file for complete search history.

(56) References Cited

U.S. PATENT DOCUMENTS

| | | |
|---|---|---|
| 6,351,273 B1 | 2/2002 | Lemelson et al. |
| 6,943,754 B2 | 9/2005 | Aughey et al. |
| 7,488,294 B2 | 2/2009 | Torch |
| 7,815,311 B2 | 10/2010 | Johns et al. |
| 8,342,687 B2 | 1/2013 | Blixt et al. |
| 8,594,374 B1 | 11/2013 | Bozarth |
| 8,624,994 B2 | 1/2014 | Kaneda et al. |
| 8,830,142 B1 | 1/2014 | Kim et al. |
| 8,752,963 B2 | 6/2014 | McCulloch et al. |
| 8,761,459 B2 | 6/2014 | Kaneda et al. |
| 8,836,768 B1 | 9/2014 | Rafii et al. |
| 8,854,282 B1 * | 10/2014 | Wong ....................... G06F 3/14 345/7 |
| 8,929,589 B2 | 1/2015 | Publicover et al. |
| 8,982,046 B2 | 3/2015 | Edwards et al. |
| 9,185,352 B1 | 11/2015 | Jacques |
| 9,189,095 B2 | 11/2015 | Eden et al. |
| 9,207,760 B1 | 12/2015 | Wu et al. |
| 9,253,442 B1 | 2/2016 | Pauli |
| 9,380,287 B2 | 6/2016 | Nistico et al. |
| 9,405,365 B2 | 8/2016 | Publicover et al. |
| 9,451,166 B1 | 9/2016 | Ribardo, Jr. et al. |
| 9,501,683 B1 | 11/2016 | Hatstat et al. |
| 9,529,442 B2 | 12/2016 | Cho et al. |
| 9,600,069 B2 | 3/2017 | Publicover et al. |
| 9,668,648 B2 | 6/2017 | Pfleger et al. |
| 9,672,416 B2 | 6/2017 | Zhang et al. |
| 9,693,684 B2 | 7/2017 | Lopez et al. |
| 9,727,136 B2 | 8/2017 | Willairat et al. |
| 9,737,209 B2 | 8/2017 | Gramatikov et al. |
| 9,785,233 B2 | 10/2017 | San Agustin Lopez et al. |
| 9,801,539 B2 | 10/2017 | Kerr et al. |
| 9,811,158 B2 | 11/2017 | Hennessey et al. |
| 9,851,091 B2 | 12/2017 | Im et al. |
| 9,936,195 B2 | 4/2018 | Horesh |
| 9,958,941 B2 | 5/2018 | Gustafsson et al. |
| 9,961,307 B1 | 5/2018 | Weinblatt |
| 9,977,960 B2 | 5/2018 | Gustafsson et al. |
| 10,016,131 B2 | 7/2018 | Liu et al. |
| 10,048,749 B2 | 8/2018 | Miao et al. |
| 10,114,459 B2 | 10/2018 | Algotsson et al. |
| 10,157,313 B1 | 12/2018 | Zhang et al. |
| 10,229,511 B2 | 3/2019 | Meier |
| 10,285,589 B2 | 5/2019 | Hart et al. |
| 10,303,250 B2 | 5/2019 | Jeong |
| 10,307,053 B2 | 6/2019 | Fayolle |
| 10,416,764 B2 | 9/2019 | Wanner et al. |
| 10,438,373 B2 | 10/2019 | Wang et al. |
| 10,452,137 B2 | 10/2019 | Noda et al. |
| 10,488,668 B2 | 11/2019 | Cazalet |
| 10,489,680 B2 | 11/2019 | Aliabadi et al. |
| 10,496,160 B2 | 12/2019 | Lu et al. |
| 10,514,542 B2 | 12/2019 | Erinjippurath et al. |
| 10,546,193 B2 | 1/2020 | Schmidt et al. |
| 10,546,194 B2 | 1/2020 | Tsurumi |
| 10,634,934 B2 | 4/2020 | Chene et al. |
| 10,698,205 B2 | 6/2020 | Huang |
| 10,909,711 B2 | 2/2021 | Schroeder et al. |
| 10,976,813 B2 | 4/2021 | Nistico et al. |
| 11,017,558 B2 | 5/2021 | Noble et al. |
| 11,023,038 B2 | 6/2021 | Yasuda et al. |
| 11,033,204 B2 | 6/2021 | Massonneau et al. |
| 2003/0184868 A1 | 10/2003 | Geist |
| 2004/0174496 A1 | 9/2004 | Ji et al. |
| 2005/0034287 A1 | 2/2005 | Xie |
| 2005/0225723 A1 | 10/2005 | Pilu |
| 2006/0240005 A1 | 10/2006 | Velardi |
| 2006/0279692 A1 | 12/2006 | Bruck |
| 2007/0066916 A1 | 3/2007 | Lemos |
| 2009/0190026 A1 | 7/2009 | Chen |
| 2010/0045933 A1 | 2/2010 | Eberl et al. |
| 2010/0053555 A1 | 3/2010 | Enriquez et al. |
| 2010/0220288 A1 | 9/2010 | Cleveland |
| 2012/0212593 A1 | 8/2012 | Na'aman et al. |
| 2012/0290401 A1 | 11/2012 | Neven |
| 2012/0293773 A1 | 11/2012 | Publicover et al. |
| 2013/0050070 A1 | 2/2013 | Lewis et al. |
| 2013/0066213 A1 | 3/2013 | Wellington |
| 2013/0069883 A1 | 3/2013 | Oga |
| 2013/0083976 A1 | 4/2013 | Ragland |
| 2013/0100025 A1 | 4/2013 | Vernacchia |
| 2013/0114043 A1 | 5/2013 | Balan et al. |
| 2013/0120224 A1 | 5/2013 | Cajigas et al. |
| 2013/0207887 A1 | 8/2013 | Raffle et al. |
| 2013/0222213 A1 | 8/2013 | Abdollahi et al. |
| 2013/0318776 A1 | 12/2013 | Jacobs et al. |
| 2013/0321925 A1 | 12/2013 | Jacobs et al. |
| 2014/0022371 A1 | 1/2014 | Huang et al. |
| 2014/0043581 A1 | 2/2014 | Chen |
| 2014/0049452 A1 | 2/2014 | Maltz |
| 2014/0055591 A1 | 2/2014 | Katz |
| 2014/0055746 A1 | 2/2014 | Nistico et al. |
| 2014/0055747 A1 | 2/2014 | Nistico et al. |
| 2014/0152558 A1 | 6/2014 | Salter et al. |
| 2014/0156219 A1 | 6/2014 | Soubra et al. |
| 2014/0191927 A1 | 7/2014 | Cho |
| 2014/0218281 A1 | 8/2014 | Amayeh et al. |
| 2014/0226131 A1 | 8/2014 | Lopez et al. |
| 2014/0247232 A1 | 9/2014 | George-Svahn et al. |
| 2014/0285404 A1 | 9/2014 | Takano et al. |
| 2014/0347456 A1 * | 11/2014 | Kato ................... H04N 13/332 348/59 |
| 2014/0354953 A1 | 12/2014 | Chen et al. |
| 2015/0070470 A1 | 3/2015 | McMurrough |
| 2015/0085251 A1 | 3/2015 | Larsen |
| 2015/0169050 A1 | 6/2015 | Publicover et al. |
| 2015/0181100 A1 | 6/2015 | Publicover et al. |
| 2015/0302585 A1 | 10/2015 | VanBlon et al. |
| 2015/0310263 A1 | 10/2015 | Zhang et al. |
| 2016/0004306 A1 | 1/2016 | Maltz |
| 2016/0005176 A1 | 1/2016 | Nguyen et al. |
| 2016/0011658 A1 | 1/2016 | Lopez et al. |
| 2016/0166190 A1 | 1/2016 | Publicover et al. |
| 2016/0109945 A1 | 4/2016 | Kempinski |
| 2016/0126675 A2 | 5/2016 | Daoura |
| 2016/0166146 A1 | 6/2016 | Sarkar |
| 2016/0187969 A1 | 6/2016 | Larsen et al. |
| 2016/0202756 A1 | 7/2016 | Wu et al. |
| 2016/0206196 A1 | 7/2016 | Pfleger et al. |
| 2016/0224110 A1 | 8/2016 | Massonneau et al. |
| 2016/0246367 A1 | 8/2016 | Fungare et al. |
| 2016/0252751 A1 | 9/2016 | Kim |
| 2016/0262608 A1 | 9/2016 | Krueger |
| 2016/0267708 A1 | 9/2016 | Nistico et al. |
| 2016/0286110 A1 | 9/2016 | Ribardo, Jr. et al. |
| 2016/0328016 A1 | 11/2016 | Andersson et al. |
| 2017/0004363 A1 | 1/2017 | Dore et al. |
| 2017/0017299 A1 | 1/2017 | Biedert et al. |
| 2017/0031437 A1 | 2/2017 | Qian et al. |

(56) References Cited

U.S. PATENT DOCUMENTS

| | | | |
|---|---|---|---|
| 2017/0035293 | A1 | 2/2017 | Nistico et al. |
| 2017/0038607 | A1 | 2/2017 | Camara |
| 2017/0116476 | A1 | 4/2017 | Publicover et al. |
| 2017/0123491 | A1 | 5/2017 | Hansen |
| 2017/0136626 | A1 | 5/2017 | Wang et al. |
| 2017/0176778 | A1 | 6/2017 | Ushakov |
| 2017/0188823 | A1 | 7/2017 | Ganesan et al. |
| 2017/0243387 | A1 | 8/2017 | Li et al. |
| 2017/0276934 | A1 | 9/2017 | Sarkar |
| 2017/0308734 | A1 | 10/2017 | Chalom et al. |
| 2017/0332901 | A1 | 11/2017 | Hwang et al. |
| 2017/0351326 | A1 | 12/2017 | Aarts et al. |
| 2017/0363885 | A1 | 12/2017 | Blum et al. |
| 2017/0372487 | A1 | 12/2017 | Lagun et al. |
| 2018/0018451 | A1 | 1/2018 | Spizhevoy et al. |
| 2018/0032131 | A1 | 2/2018 | Yasuda et al. |
| 2018/0059782 | A1 | 3/2018 | San Agustin et al. |
| 2018/0089834 | A1 | 3/2018 | Spizhevoy et al. |
| 2018/0095295 | A1 | 4/2018 | Chene et al. |
| 2018/0103194 | A1 | 4/2018 | Tang |
| 2018/0103903 | A1 | 4/2018 | Tzvieli et al. |
| 2018/0137358 | A1 | 5/2018 | Rousseau et al. |
| 2018/0157045 | A1 | 6/2018 | Davami |
| 2018/0157892 | A1 | 6/2018 | Han et al. |
| 2018/0180893 | A1 | 6/2018 | Gupta |
| 2018/0181809 | A1 | 6/2018 | Ranjan et al. |
| 2018/0267604 | A1 | 9/2018 | Bhattacharya |
| 2018/0286070 | A1 | 10/2018 | Benedetto |
| 2019/0005679 | A1 | 1/2019 | Nie |
| 2019/0043216 | A1 | 2/2019 | Yabuuchi et al. |
| 2019/0076015 | A1 | 3/2019 | Johansson et al. |
| 2019/0080474 | A1 | 3/2019 | Lagun et al. |
| 2019/0082170 | A1 | 3/2019 | Akahori |
| 2019/0086669 | A1 | 3/2019 | Percival et al. |
| 2019/0087973 | A1 | 3/2019 | Kaehler et al. |
| 2019/0156100 | A1 | 5/2019 | Rougeaux et al. |
| 2019/0265788 | A1 | 8/2019 | Yosha et al. |
| 2020/0183190 | A1 | 6/2020 | Rousseau et al. |
| 2020/0335065 | A1 | 10/2020 | Furuta et al. |
| 2020/0364453 | A1 | 11/2020 | Tonsen et al. |
| 2021/0041701 | A1 | 2/2021 | Kassner et al. |
| 2021/0049410 | A1 | 2/2021 | Dierkes et al. |
| 2021/0247617 | A1 | 8/2021 | Kassner et al. |

FOREIGN PATENT DOCUMENTS

| | | |
|---|---|---|
| CN | 102930252 | 2/2013 |
| CN | 103356163 | 10/2013 |
| CN | 105676456 | 6/2016 |
| CN | 106599994 | 4/2017 |
| CN | 206805020 | 12/2017 |
| CN | 107545302 | 1/2018 |
| CN | 107564062 | 1/2018 |
| CN | 109254420 | 1/2019 |
| CN | 109298533 | 2/2019 |
| CN | 109820524 | 5/2019 |
| DE | 19807902 | 9/1999 |
| DE | 102009049849 | 4/2011 |
| DE | 10 2010 018 562 | 10/2011 |
| DE | 10 2014 206 623 | 10/2015 |
| DE | 10 2016 210 288 | 12/2017 |
| EP | 1403680 | 3/2004 |
| EP | 1755441 | 2/2007 |
| EP | 1027627 | 2/2009 |
| EP | 2096577 | 9/2009 |
| EP | 2309307 | 4/2011 |
| EP | 2416280 | 2/2012 |
| EP | 2490155 | 8/2012 |
| EP | 2573650 | 3/2013 |
| EP | 2784632 | 10/2014 |
| EP | 2805671 | 11/2014 |
| EP | 2886041 | 6/2015 |
| EP | 2795888 | 9/2015 |
| EP | 2940555 | 11/2015 |
| EP | 2943835 | 11/2015 |
| EP | 2956844 | 12/2015 |
| EP | 2980628 | 2/2016 |
| EP | 3005030 | 4/2016 |
| EP | 3047883 | 7/2016 |
| EP | 3059629 | 8/2016 |
| EP | 3112922 | 1/2017 |
| EP | 3129849 | 2/2017 |
| EP | 3135464 | 3/2017 |
| EP | 3137938 | 3/2017 |
| EP | 3228238 | 10/2017 |
| EP | 3236338 | 10/2017 |
| EP | 3252566 | 12/2017 |
| EP | 3258308 | 12/2017 |
| EP | 3267295 | 2/2018 |
| EP | 3305176 | 4/2018 |
| EP | 3305179 | 4/2018 |
| EP | 3376163 | 9/2018 |
| EP | 3460785 | 3/2019 |
| EP | 3521911 | 8/2019 |
| FR | 3081565 | 11/2019 |
| TW | M401786 | 4/2011 |
| WO | 9905988 | 2/1999 |
| WO | 9926126 | 5/1999 |
| WO | 2005009466 | 2/2005 |
| WO | 2005094667 | 10/2005 |
| WO | 2007/016739 | 2/2007 |
| WO | 2009043927 | 4/2009 |
| WO | 2010071928 | 7/2010 |
| WO | 2011/144932 | 11/2011 |
| WO | 2012052061 | 4/2012 |
| WO | 2013059940 | 5/2013 |
| WO | 2013067230 | 5/2013 |
| WO | 2014/033306 | 3/2014 |
| WO | 2014085789 | 6/2014 |
| WO | 2014186620 | 11/2014 |
| WO | 2015024031 | 2/2015 |
| WO | 2015/051834 | 4/2015 |
| WO | 2015/072202 | 5/2015 |
| WO | 2015/179253 | 11/2015 |
| WO | 2016025583 | 2/2016 |
| WO | 2016074861 | 5/2016 |
| WO | 2016078911 | 5/2016 |
| WO | 2016097919 | 6/2016 |
| WO | 2016111880 | 7/2016 |
| WO | 2016146486 | 9/2016 |
| WO | 2016146488 | 9/2016 |
| WO | 2017001146 | 1/2017 |
| WO | 2017025486 | 2/2017 |
| WO | 2017027352 | 2/2017 |
| WO | 2017/046419 | 3/2017 |
| WO | 2017053966 | 3/2017 |
| WO | 2017053971 | 3/2017 |
| WO | 2017053972 | 3/2017 |
| WO | 2017053974 | 3/2017 |
| WO | 2017/096396 | 6/2017 |
| WO | 2017151206 | 9/2017 |
| WO | 2017/216118 | 12/2017 |
| WO | 2018000020 | 1/2018 |
| WO | 2018000039 | 1/2018 |
| WO | 2018063451 | 4/2018 |
| WO | 2018149875 | 8/2018 |

OTHER PUBLICATIONS

Safaee-Rad, R., Tchoukanov, I., Smith, K., & Benhabib, B. (1992). "Three-dimensional location estimation of circular features for machine vision", IEEE Transactions on Robotics and Automation, 8(5), 624 640.

Dierkes, Kassner, Bulling: "A novel approach to single camera, glint-free 3D eye model fitting including corneal refraction". Proc. ETRA Warsaw/Poland Jun. 2018.

Dierkes, Kassner, Bulling: "A fast approach to refraction-aware eye-model fitting and gaze prediction", Proc. ETRA Denver/USA Jun. 25-28, 2019.

Non-Final Office Action dated Apr. 14, 2021 in U.S. Appl. No. 16/967,090. (126).

Notice of Allowance dated Jul. 21, 2021 in U.S. Appl. No. 16/967,090. (126).

(56) References Cited

OTHER PUBLICATIONS

Notice of Allowance dated Oct. 20, 2021 in U.S. Appl. No. 16/967,090. (126).
Non-Final Office Action dated Dec. 17, 2021 in U.S. Appl. No. 16/967,304. (127).
Non-Final Office Action dated Jun. 23, 2021 in U.S. Appl. No. 16/967,323 (128).
Final Office Action dated Nov. 5, 2021 in U.S. Appl. No. 16/967,323 (128).
Non-Final Office Action dated Jan. 27, 2022 in U.S. Appl. No. 16/967,323 (128).
Non-Final Office Action dated Jun. 24, 2021 in U.S. Appl. No. 16/967,363 (129).
Final Office Action dated Jan. 6, 2022 in U.S. Appl. No. 16/967,363 (129).
Krafka, Building Real-Time Unconstrained, Eye Tracking with Deep Learning, B.S., University of Georgia, Dec. 2015. (112 pgs.).
Krafka, et al., "Eye Tracking for Everyone", University of Georgia, pp. 2176-2184, 2016. (9 pgs.).
Abstract Book—CVPR—2016 Main Conference and Workshops, 2016.
Notice of Allowance dated Mar. 30, 2022 in U.S. Appl. No. 16/967,304.
Moritz Kassner, Will Patera, Andreas Bulling: "Pupil: An Open Source Platform for Pervasive Eye Tracking and Mobile Gaze-based Interaction", Proceedings of the 2014 ACM International Joint Conference on Pervasive and Ubiquitous Computing: Adjunct Publication, pp. 1151-1160, ACM Sep. 13-17, 2014.
Marc Tonsen, Andreas Bulling et al.: "InvisibleEye: Mobile Eye Tracking Using Multiple Low-Resolution Cameras and Learning-Based Gaze Estimation", Proceedings of the ACM on Interactive, Mobile, Wearable and Ubiquitous Technologies, vol. 1, No. 3, Article 106, Sep. 2017.
Mayberry, Addison, et al. "iShadow: design of a wearable, real-time mobile gaze tracker." Proceedings of the 12th annual international conference on Mobile systems, applications, and services, p. 82-94, ACM, 2014.
Mayberry PhD thesis, Leveraging Eye Structure and Motion to Build a Low-Power Wearable Gaze Tracking System, Oct. 2018.
Ishiguro, Yoshio, et al. "Aided eyes: eye activity sensing for daily life." Proceedings of the 1st Augmented Human International Conference. ACM, 2010.
Fuhl, Wolfgang, et al. "PupilNet: convolutional neural networks for robust pupil detection." arXiv preprint arXiv:1601.04902 (2016).

Baluja, Shumeet, and Dean Pomerleau. "Non-intrusive gaze tracking using artificial neural networks" Advances in Neural Information Processing Systems. 1994.
Pomplun et al. "An artificial neural network for high precision eye movement tracking", Advances in Artificial Intelligence, vol. 861 of the series Lecture Notes in Computer Science, pp. 63-69. 2005.
Zhang, Xucong, et al. "Appearance-based gaze estimation in the wild." Proceedings of the IEEE Conference on Computer Vision and Pattern Recognition. 2015.
Zhang, Xucong, et al. "It's written all over your face: Full-face appearance-based gaze estimation." Computer Vision and Pattern Recognition Workshops (CVPRW), 2017 IEEE Conference on. IEEE, 2017.
Feng Lu, Yusuke Sugano, Takahiro Okabe, and Yoichi Sato: "Adaptive Linear Regression for Appearance-Based Gaze Estimation", IEEE transactions on pattern analysis and machine intelligence (TPAMI) 36, 10 (2014), 2033-2046.
Cihan Topal, Serkan Gunal, Onur Kodeviren, Atakan Dogan, and Omer N Gerek: "A Low-Computational Approach on Gaze Estimation With Eye Touch System", IEEE transactions on Cybernetics 44, 2 (2013), 228-239.
Krafka, et al. "Eye tracking for everyone." IEEE Conference on Computer Vision and Pattern Recognition (CVPR), pp. 2176-2184, 2016.
Sugano, Bulling: "Self-calibrating head-mounted eye trackers using egocentric visual saliency." In Proc. ACM Symposium on User Interface Software and Technology (UIST 2015). 363-372.
Huang, Veeraraghavan, Sabharwal: "TabletGaze: Unconstrained appearance-based gaze estimation in mobile tablets" Jul. 16, 2016.
Hickson et al., "Eyemotion: Classifying facial expressions in VR using eye-tracking cameras", arXiv:1707.07204v2 [cs.CV] Jul. 28, 2017.
Anjith George, Aurobinda Routray: "Real-time Eye Gaze Direction Classification Using Convolutional Neural Network", IEEE InternationalConference on Signal Processing and Communication, SPCOM 2016.
Olszewski, K., Lim, J., Saito, S., Li, H.: "High-Fidelity Facial and Speech Animation for VR HMDs". ACM Trans. Graph.35, 6, Article 221 (Nov. 2016).
"Pogocam", Youtube, Jan. 6, 2017, URL: https://www.youtube.com/watc67v=pHumrhISYx4.
Santini, Fuhl, Kasneci: "CalibMe: Fast and Unsupervised Eye Tracker Calibration for Gaze-Based Pervasive Human-Computer Interaction", Proc. CHI 2017, May 6-11, 2017.
Bace, Staal, Sörös: "Wearable Eye Tracker Calibration at Your Fingertips", Proc. ETRA 2018, Jun. 14-17, 2018, Warsaw/Poland.

* cited by examiner

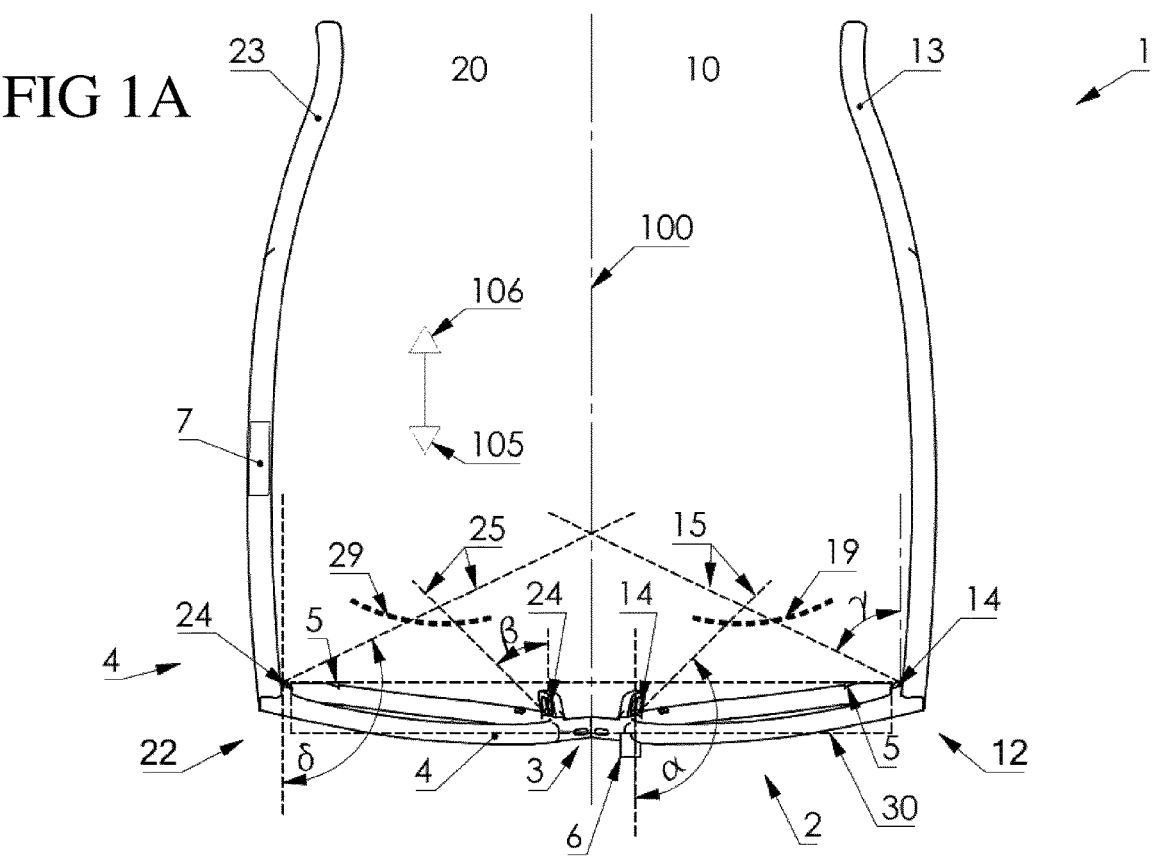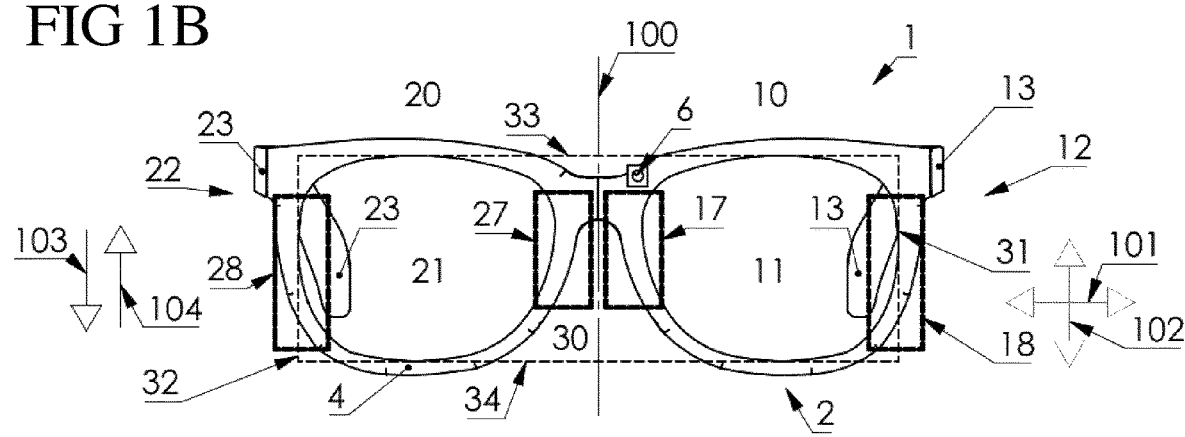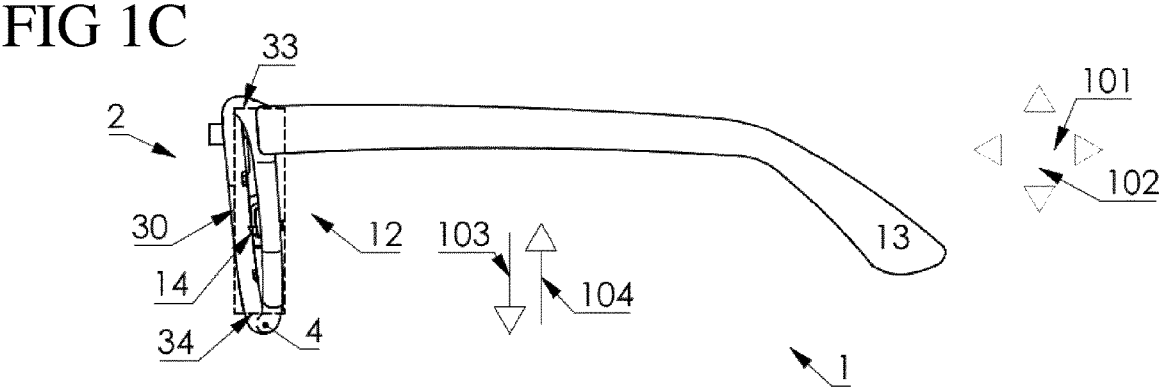

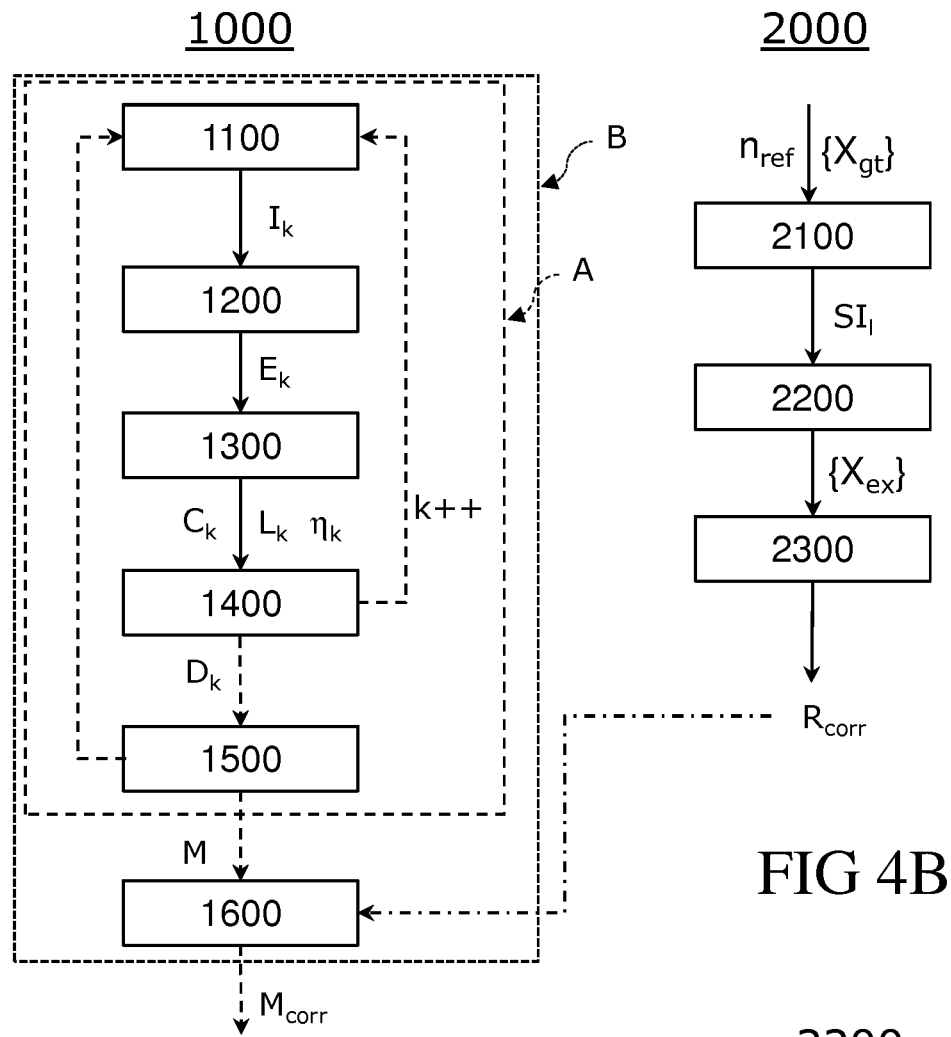
FIG 4A
FIG 4B
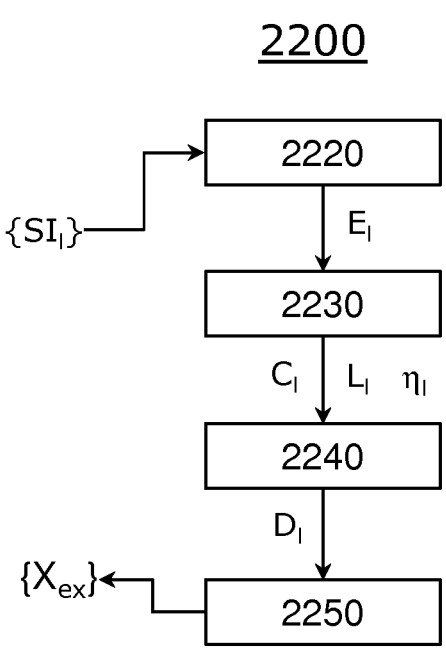
FIG 4C

DEVICES, SYSTEMS AND METHODS FOR PREDICTING GAZE-RELATED PARAMETERS

CROSS-REFERENCE TO RELATED APPLICATIONS

This Utility Patent Application claims priority under 35 U.S.C. § 371 to International Application Serial No. PCT/EP2019/064656 filed Jun. 5, 2019, which is incorporated herein by reference in its entirety.

TECHNICAL FIELD

Embodiments of the present invention relate to a method for generating data suitable for determining a parameter of a human eye, in particular a method for generating the data suitable for determining the parameter of the human eye using a head-wearable device, a method for determining a correction function for the parameter, and a system comprising a head-wearable device having a camera for taking images of a user's eye.

BACKGROUND

Over the last decades, camera-based eye trackers have become a potent and wide-spread research tool in many fields including human-computer interaction, psychology, and market research. Offering increased mobility compared to remote eye-tracking solutions, head-mounted eye trackers, in particular, have enabled the acquisition of gaze data during dynamic activities also in outdoor environments. Remote eye trackers typically rely on complex optical setups involving the active generation of corneal reflections (so called "glints") by means of infrared (IR) LEDs and/or pairs of calibrated stereo cameras. Glint-based (i.e. using corneal reflections) gaze estimation needs to reliably detect those reflections in the camera image and needs to be able to associate each with a unique light source. If successful, the 3D position of the cornea center (assuming a known radius of curvature) can be determined. Beside hardware requirements, one issue encountered in this approach are spurious reflections produced by other illuminators, which may strongly impact the achievable accuracy. Due to the technical infeasibility of robustly porting such solutions to head-mounted eye trackers, the latter are desired to resolve ambiguities during parameter estimation with more restricted hardware setups. From an engineering point of view, glint-free estimation of gaze-related and other parameters of a human eye using a single near-eye camera is highly desirable. However, determining of human eye parameters from images taken with a single near-eye camera (solving an inverse problem) is challenging and so far requires comparatively high computing power often limiting the application area, in particular if "slippage" of the eye tracker is to be compensated.

Accordingly, there is a need to further improve the speed and accuracy of the detection of gaze direction and other gaze-related parameters of the human eye and reduce the computational effort required therefor.

SUMMARY

According to an embodiment of a method for generating data suitable for determining a parameter of a human eye having an eyeball and an iris defining a pupil, the method includes receiving a first image of the eye for a first time from a camera defining an image plane and being of known camera intrinsics. A first ellipse at least substantially representing a border of the pupil at the first time is determined in the first image. The known camera intrinsics and the ellipse are used to determine an orientation vector of a first circle and a first center line on which a center of the first circle is located, so that a projection of the first circle, in a direction parallel to the first center line, onto the image plane is expected to reproduce the first ellipse. A first eye intersecting line expected to intersect a center of the eyeball at the first time is determined as a line which is, in the direction of the orientation vector, parallel-shifted to the first center line by an expected distance between the center of the eyeball and a center of the pupil.

According to an embodiment of a method for generating data for determining a correction function for at least one parameter of a human eye which is derivable from at least one image of the human eye taken with a camera of known camera intrinsics, the method includes calculating, using the known camera intrinsics, synthetic camera images of several model eyeballs of the human eye with varying effective corneal refraction index, for a plurality of given values of the at least one parameter of the model eyeballs. The synthetic camera images are used to determine expected values of the at least one parameter. The expected values of the at least one parameter and the given values of the at least one parameter are used to determine a correction function which maps, depending on the effective corneal refraction index, the expected values of the at least one parameter to the respective given values of the at least one parameter.

According to an embodiment of a system, the system comprises a head-wearable device and a computing and control unit, the head-wearable device includes a camera for taking images of an eye of a user wearing the head-wearable device. The eye includes an eyeball and an iris defining a pupil. The camera intrinsics of the camera are known. The camera includes a sensor defining an image plane of the camera. The computing and control unit is configured to receive from the camera a first image of the eye of the user taken at a first time, to determine a first ellipse in the first image, the first ellipse at least substantially representing a border of the pupil at the first time, to use the known camera intrinsics and the first ellipse to determine an orientation vector of a first circle and a first center line on which a center of the first circle is located, so that a projection of the first circle, in a direction parallel to the first center line, onto the image plane is expected to reproduce the first ellipse, and to determine a first eye intersecting line expected to intersect a center of the eyeball at the first time as a line which is, in the direction of the orientation vector, parallel-shifted to the first center line by an expected distance between the center of the eyeball and a center P of the pupil.

Other embodiments include (non-volatile) computer-readable storage media or devices, and one or more computer programs recorded on one or more computer-readable storage media or computer storage devices. The one or more computer programs can be configured to perform particular operations or processes by virtue of including instructions that, when executed by one or more processors of a system, in particular a system comprising the head-wearable devices as explained herein, cause the system to perform the operations or processes.

Those skilled in the art will recognize additional features and advantages upon reading the following detailed description, and upon viewing the accompanying drawings.

BRIEF DESCRIPTION OF THE DRAWINGS

The components in the figures are not necessarily to scale, instead emphasis being placed upon illustrating the principles of the invention. Moreover, in the figures, like reference numerals designate corresponding parts. In the drawings:

FIG. 1A illustrates a top view of a head-wearable device according to an embodiment;

FIG. 1B shows the front view on the head-wearable device according to FIG. 1A;

FIG. 1C is a lateral view on head-wearable device according to FIG. 1A;

FIG. 4A illustrates a flow chart of a method for generating data suitable for determining a parameter of a human eye according to embodiments;

FIG. 4B illustrates a flow chart of a method for determining a correction function according to embodiments;

FIG. 4C illustrates a flow chart of a method for determining a correction function according to embodiments;

DETAILED DESCRIPTION

Figure 2A:
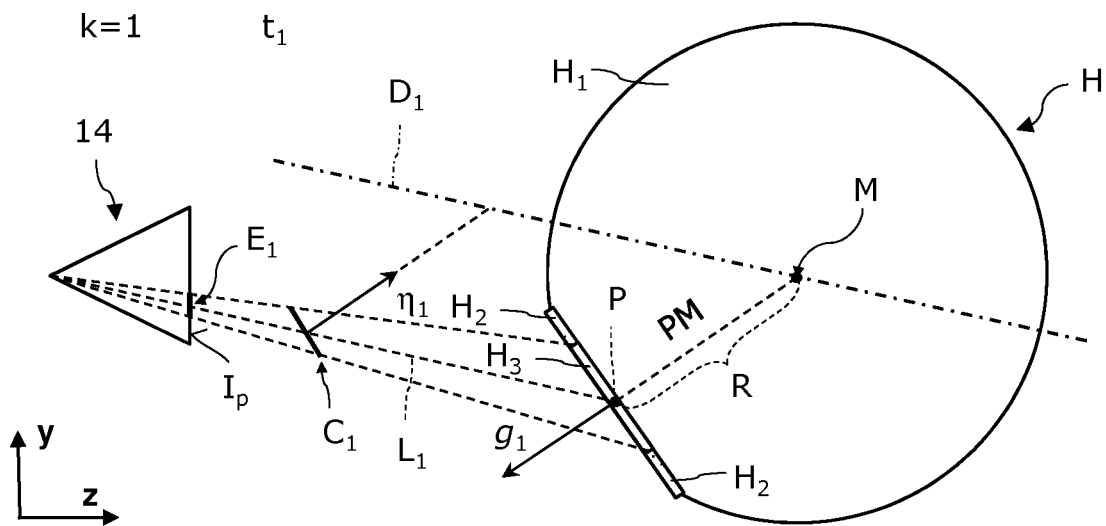
FIG. 2A to 2C illustrates processes used in a method for generating data suitable for determining a parameter of a human eye according to embodiments.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is a task of the invention to provide methods, systems and devices allowing for improved generating, in particular computationally faster, easier and/or more reliably generating of data suitable for determining parameters of a human eye using a head-wearable device including an eye camera for generating images of a respective eye of a user wearing the head-wearable device.

Said tasks are solved by the subject matter of the independent claims.

The head-wearable device is configured for being wearable on a user's head and may be used for determining one or more gaze-related parameters of a user wearing the head-wearable device.

The head-wearable device may be implemented as (head-wearable) spectacles device comprising a spectacles body, which is configured such that it can be worn on a head of a user, for example in a way usual glasses are worn. Hence, the spectacles device when worn by a user may in particular be supported at least partially by a nose area of the user's face. The head-wearable device may also be implemented as an augmented reality (AR-) and/or virtual reality (VR-) device (AR/VR headset), in particular a goggles, an AR head-wearable display, and a VR head-wearable display. For the sake of clarity, head-wearable devices are mainly described with regard to head-wearable spectacles devices in the following.

This state of usage of the head-wearable (spectacles) device being arranged at the user's face will be further defined as the "intended use" of the spectacles device, wherein direction and position references, for example horizontal and vertical, parallel and perpendicular, left and right, front and back, up and down, etc., refer to this intended use. As a consequence, lateral positions as left and right, an upper and lower position, and a front/forward and back/backward are to be understood from user's usual view. Equally, this applies to a horizontal and vertical orientation, wherein the user's head during the intended use is in a normal, hence upright, non-tilted, non-declined and non-nodded position.

The spectacles body (main body) typically includes a left ocular opening and a right ocular opening, which mainly come with the functionality of allowing the user to look through these ocular openings. Said ocular openings can be embodied, but not limited to, as sunscreens, optical lenses or non-optical, transparent glasses or as a non-material, optical pathway allowing rays of light passing through.

The spectacles body may, at least partially or completely, form the ocular openings by delimiting these from the surrounding. In this case, the spectacles body functions as a frame for the optical openings. Said frame is not necessarily required to form a complete and closed surrounding of the ocular openings. Furthermore, it is possible that the optical openings themselves have a frame like configuration, for example by providing a supporting structure with the help of transparent glass. In the latter case, the spectacles device has the form similar to frameless glasses, wherein only a nose support/bridge portion and ear-holders are attached to the glass screens, which therefore serve simultaneously as an integrated frame and as optical openings.

In addition, a middle plane of the spectacles body may be identified. In particular, said middle plane describes a structural centre plane of the spectacles body, wherein respective structural components or portions, which are comparable or similar to each other, are placed on each side of the middle plane in a similar manner. When the spectacles device is in intended use and worn correctly, the middle plane coincides with a median plane of the user.

Further, the spectacles body typically includes a nose bridge portion, a left lateral portion and a right lateral portion, wherein the middle plane intersects the nose bridge portion, and the respective ocular opening is located between the nose bridge portion and the respective lateral portion.

For orientation purposes, a plane being perpendicular to the middle plane shall be defined, which in particular is oriented vertically, wherein said perpendicular plane is not necessarily firmly located in a defined forward or backward position of the spectacles device.

The head-wearable device has an eye camera having a sensor arranged in or defining an image plane for taking images of a first eye of the user, i.e. of a left or a right eye of the user. In other words, the eye camera, which is in the following also referred to as camera and first eye camera, may be a left eye camera or a right (near-) eye camera. The eye camera is typically of known camera intrinsics.

As used herein, the term "camera of known camera intrinsics" shall describe that the optical properties of the camera, in particular the imaging properties (imaging characteristics) of the camera are known and/or can be modelled using a respective camera model including the known intrinsic parameters (known intrinsics) approximating the eye camera producing the eye images. Typically, a pinhole camera model is used for modelling the eye camera. The known intrinsic parameters may include a focal length of the camera, an image sensor format of the camera, a principal point of the camera, a shift of a central image pixel of the camera, a shear parameter of the camera, and/or one or more distortion parameters of the camera.

In addition, the head-wearable device may have a further eye camera of known camera intrinsics for taking images of a second eye of the user, i.e. of a right eye or a left eye of the user. In the following the further eye camera is also referred to as further camera and second eye camera.

In other words, the head-wearable device may, in a binocular setup, have a left and a right (eye) camera, wherein the left camera serves for taking a left image or a stream of images of at least a portion of the left eye the user, and wherein the right camera takes an image or a stream of images of at least a portion of a right eye of the user.

Typically, the first and second eye cameras have the same camera intrinsics (are of the same type). Accordingly, generating of data suitable for determining (a) parameter(s) of the user's eyes may be unified.

However, apart from a few exceptions referring to 3D gaze points of the eyes as human eye parameter, the methods explained herein refer to one eye and are thus applicable in a monocular setup having one (near) eye camera only.

The parameter of the human eye typically refers to an eyeball the human eye and/or a pupil of the human eye.

In particular, the parameter of the human eye may refer to and/or be a center of the eyeball, in particular a center of rotation of the eyeball or an optical center of the eyeball, and/or a gaze related parameter of the human eye(s).

The gaze-related parameter may be a gaze-direction related parameter, a pupil area, a pupil size, a pupil diameter, a pupil radius, an iris diameter, a cornea characteristic of at least one eye, a cornea radius, an eyeball radius, a distance pupil-center to cornea-center, a distance pupil-center to eyeball-center, a distance pupil-center to limbus center, a cornea keratometric index of refraction, a cornea index of refraction, a vitreous humor index of refraction, a distance crystalline lens to eyeball-center, to cornea center and/or to corneal apex, a crystalline lens index of refraction, a degree of astigmatism, a limbus major and/or minor axes orientation, an eye cyclo-torsion, an eye intra-ocular distance, an eye vergence, a statistics over eye adduction and/or eye abduction, and a statistics over eye elevation and/or eye depression, data about drowsiness and/or awareness of the user, parameters for user iris verification and/or identification.

The gaze-direction related parameter may be a gaze direction, a cyclopean gaze direction, a 3D gaze point, a 2D gaze point, a visual axis orientation, an optical axis orientation, a pupil axis orientation, and a line of sight orientation of the user.

The gaze-direction related parameter(s) is/are typically determined with respect to a coordinate system that is fixed to the eye camera(s) and/or the head-wearable device.

For example, a Cartesian coordinate system defined by the image plane of the eye camera(s) may be used.

Points and directions may also be specified within and/or converted into a device coordinate system, a head coordinate system, a world coordinate system or any other suitable coordinate system.

The eye camera(s) can be arranged at the spectacles body in inner eye camera placement zones and/or in outer eye camera placement zones, in particular wherein said zones are determined such, that an appropriate picture of at least a portion of the respective eye can be taken for the purpose of determining one or more a gaze-related parameter; in particular, the cameras are arranged in a nose bridge portion and/or in a lateral edge portion of the spectacles frame such, that an optical field of a respective eye is not obstructed by the respective camera. The optical field is defined as being obstructed, if the camera forms an explicitly visible area/portion within the optical field, for example if the camera points out from the boundaries of the visible field into said field, or by protruding from the boundaries into the field. For example, the cameras can be integrated into a frame of the spectacles body and thereby being non-obstructive. In the context of the present invention, a limitation of the visible field caused by the spectacles device itself, in particular by the spectacles body or frame is not considered as an obstruction of the optical field.

Furthermore, the head-wearable device may have illumination means for illuminating the left and/or right eye of the user, in particular if the light conditions within an environment of the spectacles device are not optimal.

Typically, a frame of the spectacles body is essentially symmetrical to the middle plane, wherein only minor areas, portions or elements of the frame are non-symmetrical.

In one embodiment, a method for generating data suitable for determining a parameter of a human eye includes receiving a first image of the human eye from a camera of known camera intrinsics. The first image is taken at a first time with an image sensor defining an image plane of the camera. A first ellipse representing a border of a pupil of the human eye at the first time is determined in the first image. The camera intrinsics and the ellipse are used to determine (in 3D space) an orientation vector of a first circle and a first center line on which a center of the first circle is located, so that a projection of the first circle, in a direction parallel to the first center line, onto the image plane is expected to reproduce the first ellipse at least substantially, i.e. reproduces the first ellipse with high accuracy, i.e. with a an error of less than 5% or even less than 2%. A first eye intersecting line expected to intersect a center of the eyeball of the human eye at the first time is determined as a line which is, in the direction of the orientation vector, parallel-shifted to the first center line by an expected distance between the center of the eyeball and a center of the pupil.

Accordingly, the first eye intersecting line, which limits the position of the center of the eyeball to a line and thus can be considered as a parameter of the human eye, can be determined without using glints or markers and with low calculation costs, low numerical effort and/or very fast. This even allows determining the parameters of a human eye in real time (within sub-milliseconds range per processed image) with comparatively low hardware requirements. Accordingly, parameter(s) of the human eye may be determined with hardware that is integrated into the head-wearable device during taking eye images with the camera of the head-wearable device and with a negligible delay only, respectively with hardware of low computational power, like smart devices, connectable to the head-wearable device.

Note that the process of determining the orientation vector of the first circle and the first center line is typically done similar as explained in reference [1]. Reference [1] describes a method of 3D eye model fitting and gaze estimation based on pupil shape derived from (monocular) eye images. Starting from a camera image of an eye and having determined the area of the pupil represented by an ellipse, the first step is to determine the circle in 3D space, which gives rise to the observed elliptical image pupil, assuming a (full) perspective projection and known camera parameters. If this circle is found, it can serve as an approximation of the actual pupil of the eye, i.e. the approximately circular opening of varying size within the iris. Mathematical methods for achieving this "unprojection" give rise to two ambiguities: firstly, there are two solution circles for a given fixed circle radius on the cone which represents the space of all possible solutions. Deciding which one is a correct pupil candidate is described in reference [1]. The second ambiguity is a size-distance ambiguity: given only a 2D image it is not possible to know a priori whether the pupil is small and close to the camera or large and far away from the camera. The second ambiguity is resolved in reference [1] by generating a model which comprises 3+3N parameters, including the 3 eyeball center coordinates and parameters of pupil candidates extracted from a time series of N camera images. This model is then optimized numerically in a sophisticated iterative fashion to yield the final eyeball center coordinates.

Compared to reference [1], the proposed solution herein for resolving the size-distance ambiguity (which is based on the eye intersecting line(s)) represents a considerable conceptual and computational simplification. This allows determining parameters of human eye(s) such as eyeball position (s), pupil size(s) and gaze direction(s) in real-time with considerably reduced hardware and/or software requirements. Accordingly, lightweight and/or comparatively simple head-wearable device may be more broadly used for purposes like gaze-estimation and/or pupillometry, i.e. measuring the actual size of the pupil.

Note that the method does not require taking into account a glint from the eye for generating data suitable for determining the parameter of the human eye.

In other words, the method may be glint-free. Therefore, the method does not require using structured light and/or special purpose illumination to derive parameters of the eye.

Note further that human eyes only vary in size within a very narrow margin and many physiological parameters can thus be assumed constant/equal between different persons.

For known distance R between center of the eyeball, in the following also referred to as eyeball center, and center of the pupil, in the following also referred to as pupil center, of a human, the eyeball center is, for each image/observation, expected to lie on the respectively determined eye intersecting line. For humans the distance R can be even assumed with high accuracy as a constant (R=10.39 mm). Alternatively, the distance R may be measured for humans in advance and optionally averaged. However, this is usually not required.

Each further image/observation of the eye with a different gaze direction gives rise to an independent eye intersecting line in 3D. Finding the nearest intersection of at least two independent eye intersecting lines thus yields the coordinates of the eyeball center in a non-iterative manner.

Accordingly, the method for determining a parameter of a human eye typically includes receiving a second image of the eye for a second time from the camera, more typically a plurality of further images at respective times, determining a second ellipse in the second image, the second ellipse at least substantially representing the border of the pupil at the second time, more typically determining for each of the further images a respective ellipse, using the second ellipse to determine an orientation vector of a second circle and a second center line on which a center of the second circle is located, so that a projection of the second circle, in a direction parallel to the second center line, onto the image plane is expected to reproduce the second ellipse, more typically using the respective ellipse to determine an orientation vector of the further circle and a further center line on which the further circle is located, so that a projection of the further circle, in a direction parallel to the further center line, onto the image plane is expected to reproduce the respective further ellipse, and determining a second eye intersecting line expected to intersect the center of the eyeball at the second time as a line which is, in the direction of the orientation vector of the second circle, parallel-shifted to the second center line by the expected distance, more typically determining further eye intersecting lines each of which is expected to intersect the center of the eyeball at the respective further time as a line which is, in the direction of the orientation vector of the further circle, parallel-shifted to the further center line by the expected distance.

In other words, a camera model such as a pinhole camera model describing the imaging characteristics of the camera and defining an image plane (and known camera intrinsic parameters as parameters of the camera model) is used to determine for several images taken at different times with the camera an orientation vector of a respective circle and a respective center line on which a center of the circle is located, so that a projection of the circle, in a direction parallel to the center line, onto the image plane reproduces the respective ellipse in the camera model, and determining a respective line which is, in the direction of the orientation vector, which typically points away from the camera, parallel-shifted to the center line by an expected distance between a center of an eyeball of the eye and a center of a pupil of the eye as an eye intersecting line which intersects the center of the eyeball at the first time. Thereafter, the eyeball center may be determined as nearest intersection point of the eye intersecting lines in a least squares sense.

Typically, the respective images of the eye which are used to determine the plurality of eye intersecting lines ($D_k$, k=1 ... n) are acquired with a frame rate of at least 25 frames per second (fps), more typical of at least 30 fps, more typical of at least 60 fps, and more typical of at least 120 fps or even 200 fps.

Once the eyeball center is known, other parameters of the human eye such as gaze direction and pupil radius or size can be calculated non-iteratively.

In particular, an expected gaze direction of the eye may be determined as a vector which is antiparallel to the respective circle orientation vector.

Further, the expected co-ordinates of the center of the eyeball may be used to determine for at least one of the times an expected optical axis of the eye, an expected orientation of the eye, an expected visual axis of the eye, an expected size of the pupil and/or an expected radius of the pupil.

Furthermore, at one or more later times a respective later image of the eye may be acquired by the camera and used to determine, based on the determinant respective later eye intersecting line, at the later time(s) an expected gaze direction, an expected optical axis of the eye, an expected orientation of the eye, an expected visual axis of the eye, an expected size of the pupil and/or an expected radius of the pupil.

Alternatively and/or in addition, effects of refraction by the cornea may be taken into account.

According to an embodiment, a method for determining a correction function for one or more parameter(s) of a human eye is disclosed, the method includes calculating, using known (optical) camera properties (typically including camera intrinsics) of the camera used for taking one or more image(s) of the human eye, for a plurality of given values of the one or more parameters of the model eyeballs and varying corneal refraction index synthetic camera images of several model eyeballs of the human eye. The synthetic camera images are used to determine (calculate) expected values of the one or more parameters of a human eye. The expected values and the corresponding given values of the one or more parameters are used to determine a correction function which maps, depending on the effective corneal refraction index, the expected values to the respective given values of the one or more parameters.

The given values typically include co-ordinates of respective centers of the model eyeballs, given radii of a pupil of the model eyeballs and/or given gaze directions of the model eyeballs.

Determining the expected values typically includes determining respective first eye intersecting lines expected to intersect the center of the respective model eyeball for the plurality of given co-ordinates of respective centers of the model eyeballs, given radii of a pupil of the model eyeballs and/or given gaze directions.

Determining the correction function may be achieved using a multivariate polynomial regression analysis.

Calculating the synthetic camera images may be achieved by raytracing an arrangement of a camera model, which describes the camera, and (three-dimensional) model eyeballs arranged in the field of view of the camera model.

According to embodiments, a respective two-sphere (three-dimensional) eye model may be used as model eyeballs.

For example, the so-called LeGrand eye model may be used (see also reference [1]). Alternatively, the so-called Navarro eye model may be used for modelling eyeballs (see also reference [2] for more details) and calculating synthetic images, respectively.

The model of the camera typically includes a focal length, a shift of a central image pixel, a shear parameter, and/or one or more distortion parameters of the camera.

The camera may be modelled as a pinhole camera.

Typically, the camera defines a co-ordinate system, wherein all calculations described herein are performed with respect to this co-ordinate system.

The camera may be assumed to be substantially immobile with respect to the eye on the time scales considered, at least for a few subsequent image frames.

Likewise, the center of the eyeball may be assumed to have at least substantially non-varying co-ordinates in the co-ordinate system while the respective images of the eye are acquired by the camera on the time scales considered, at least for a few subsequent image frames.

The correction function is typically stored and may later be used to correct one or more parameters of a human eye determined from respective eye images. In particular, a corrected value for the center of the eyeball of the human eye, the expected gaze direction of the human eye, the expected optical axis of the human eye, the expected orientation of the human eye, the expected visual axis of the human eye, the expected size of the pupil of the human eye, and/or the expected radius of the pupil of the human eye may be calculated using the correction function.

Note that determining the respective (pupil circle) center line as described herein is based on the unprojection of the image ellipse using the known camera model. Different thereto, determining the respective eye intersecting line is based on the thus derived centre line and an eye model, typically a 3-D eye model. In the simplest case and without correcting the corneal refraction effects, the eye model may only have one parameter, namely the expected distance R between the center of the eyeball and the center of the pupil.

According to an embodiment, a system comprises a head-wearable device and a computing and control unit, the head-wearable device including a camera of known camera intrinsics for taking images of an eye of a user wearing the head-wearable device, and a computing and control unit connected with or connectable to the camera. The camera includes a sensor defining an image plane of the camera. The computing and control unit is configured to receive from the camera a first image of the eye of the user taken at a first time, determine in the first image a first ellipse at least substantially representing a border of the pupil at the first time, to use the camera intrinsics to determine an orientation vector of a first circle and a first center line on which a center of the first circle is located, so that a projection of the first circle, in a direction parallel to the first center line, onto the image plane is expected to reproduce the first ellipse, and to determine a first eye intersecting line expected to intersect a center of the eyeball of the eye at the first time as a line which is, in the direction of the orientation vector, parallel-shifted to the first center line by an expected distance between the center of the eyeball and a center of the pupil.

Typically, the computing and control unit is configured to perform the methods for generating data suitable for determining a parameter of a human eye as explained herein.

For example, the computing and control unit may be configured to use the first eye intersecting line and a second eye intersecting line for determining expected co-ordinates of the center of the eyeball. The second eye intersecting line is typically determined by the same method used to determine the first eye intersecting line, however for a different point in time.

Different thereto, the method for determining a correction function as explained herein is typically performed by a more powerful computing device such as a desktop computer or the like.

However, the computing and control unit may be configured to use a stored correction function taking into account corneal refraction to determine in real-time a corrected value for one or more parameters of a human eye determined from eye images such as the center of the eyeball, the expected gaze direction of the eye, the expected optical axis of the eye, the expected orientation of the eye, the expected visual axis of the eye, the expected size of the pupil, and the expected radius of the pupil.

In addition, the head-wearable device may include a further eye camera for taking images of a further eye of the user. The further camera is connected to or connectable to the computing and control unit. The further camera has a sensor defining a further image plane of the further camera. The further eye has a further eyeball and a further iris defining a further pupil. In this embodiment, the computing and control unit is configured to receive from the further camera an image of the further eye of a user taken at a further time, determining an ellipse in the image, the ellipse at least substantially representing a border of the further pupil at the further time, to use the ellipse to determine an orientation vector of a circle and a center line on which a center of the circle is located, so that a projection of the circle, in a direction parallel to the center line, onto the further image plane is expected to reproduce the ellipse, and to determine an eye intersecting line expected to intersect a center of the further eyeball at the further time as a line which is, in the direction of the orientation vector of the circle, parallel-shifted to the center line by an expected distance between the center of the further eyeball and a center of the further pupil.

The expected distance between the center of the further eyeball and the center of the further pupil is at least substantially equal to the expected distance (R) between the center of the eyeball and a center of the pupil.

Further, the further time may be at least substantially equal to the first time.

Typically, several images of the further eye are taken and used to determine respective eye intersecting lines of the further eye. Furthermore, the eye intersecting lines of the further eye may, similar as explained above for the eye of the user, be used to determine co-ordinates of a center of the eyeball of the further eye and/or other parameters of the further eye and/or corrected values for the parameter(s) of the further eye.

Typically, a pose of the respective camera, i.e. a position of the respective camera and/or an orientation of the respective camera is adjustable and/or fixable with respect to a frame of the head-wearable device. In either case, a pose of the respective camera with respect to the frame may be known. In this case calculations may alternatively be performed a the coordinate-system defined by the frame.

Note that the calculations concerning the further eye may be performed in the respective co-ordinate system of the further eye camera.

For reasons of accuracy, the eye camera(s) may have a resolution of at least 320×240 pixels or 640×480 pixels. However, a smaller resolution of for example 400×400 or 200×200 or even only 128×128 or 64×64 pixels may also be sufficient for some applications.

Further, the eye camera(s) may be infrared cameras.

A right IR-light source of the head-wearable device may be used to illuminate the right eye of the user and/or a left IR-light source of the head-wearable device may be used to illuminate the left eye of the respective user in embodiments referring to IR-cameras for the left and the right eye, respectively. IR-illumination may only be used/invoked when the image quality is too low or expected to be low, for example in a dark environment. IR-illumination may also be on permanently, or always be on and only switched off to save power and/or when image quality is sufficient without illumination.

In all embodiments, the typically tiny eye camera(s) are not even noticed by the user when wearing the device.

For example, the eye camera(s) may have respective volumes of less than about 40 mm$^3$ or even 10 mm$^3$.

Placing eye camera(s) in the respective lateral portion of the spectacles body allows for a very discrete and non-obtrusive camera arrangement in the spectacles body without noticeably obstructing the visible field of the user, and ensures a beneficial view on to the eyeballs of the user.

Even further, arranging the eye camera(s) in the respective lateral portion (instead of in the nose bridge portion) has the benefit that the nose bridge portion can be kept free of additional electronics and thus can be redesigned easily to adapt to different physiognomies/ethnically differing spectacle requirements, while the lateral frame portion can stay unchanged.

In addition, the lateral portion of the spectacles body provides more space for the cameras and (illumination) electronics compared to the nose bridge portion.

The cameras and (illumination) electronics may represent heat sources, but can be kept farther away from the eyes compared to arranging them in the nose bridge portion. Accordingly, wearing comfort may be further increased even if the heat sources are comparatively weak.

In one embodiment, the head-wearable (spectacles) device is provided with electric power from a companion device of the system, in particular a mobile companion device such as a smart phone, tablet or laptop computer during operation of the spectacles device. The computing and control unit may be part of the head-wearable device, in particular integrated into the head-wearable device, or the companion device.

In embodiments referring to systems including a companion device connectable with the head-wearable device, the head-wearable spectacles device may not have an internal energy storage such as a battery. Accordingly, the head-wearable (spectacles) device may be particularly lightweight. Further, less heat may be produced during device operation compared to a device with an internal (rechargeable) energy storage. This may also improve comfort of wearing.

In other embodiments, the head-wearable (spectacles) device may have a lightweight (typically less than 50 g or even 20 g or even 10 g or even 5 g) internal energy storage with a low capacity of typically not more than 200 mAh, in particular not more than 100 mAh, in particular not more than 40 mAh for feeding an internal clock, supplying the electric components of the head-wearable (spectacles device) with electric power for a short time of typically at most one min, saving the images, and/or shutting down the head-wearable (spectacles) device in case the connection to the companion device is lost or the companion device is running low of energy.

The connector for power supply and/or data exchange may be arranged at a dorsally pointed end of the left holder or the right holder.

The integrated computing and control unit typically includes an interface board (interface controller) for communicating with the companion device, for example a USB-hub board (controller).

The integrated computing and control unit may be implemented as control and processing unit also configured for calculating gaze-related parameter(s) of the user, typically even in real time or near real time, i.e. at most within 100 ms or 50 ms, more typically at most 20 ms or even at most 5 ms.

The computing and control unit of the head-wearable (spectacles) device is typically arranged non-visible within the spectacles body, in particular in the left lateral portion, in the right lateral portion, in the left holder and/or in the right holder. The control and/or processing unit (controller) of the head-wearable (spectacles) device may comprise several interconnected parts arranged in different portions of the spectacles body, for example also in the spectacles frame.

The computing and control unit of the head-wearable (spectacles) device may have a USB-hub board, a camera controller board connected with the camera, and a power-IC connected with the camera controller board, the camera and/or the connector for power supply and/or data exchange, in particular a low power SoC (System-on-Chip) for controlling and processing, and an optional head orientation sensor having an inertial measurement unit (IMU). The low power SoC may have a CPU, RAM (Random-Access Memory) as well as non-volatile memory, such as ROM (read only memory), PROM (programmable read only memory) and flash memory, a DSP and/or even a GPU.

All this can be achieved with a lightweight, unobtrusive, very comfortable head-wearable (spectacles) device that may be comparatively easy and cost-effective manufactured and repaired (easy and quick assembly/disassembly is even possible for a normal user) and can even be used as normal glasses (with standard optical lenses) or sun glasses (with detached scene camera(s)) without being easily recognized as an eye tracking device.

Furthermore, no particular heat management, physical shields to protect the user, vents or the like are required.

Reference will now be made in detail to various embodiments, one or more examples of which are illustrated in the figures. Each example is provided by way of explanation, and is not meant as a limitation of the invention. For example, features illustrated or described as part of one embodiment can be used on or in conjunction with other embodiments to yield yet a further embodiment. It is intended that the present invention includes such modifications and variations. The examples are described using specific language which should not be construed as limiting the scope of the appended claims. The drawings are not scaled and are for illustrative purposes only. For clarity, the same elements or manufacturing steps have been designated by the same references in the different drawings if not stated otherwise.

With reference to FIGS. 1A to 1C, a generalised embodiment of a head-wearable spectacles device for determining one or more gaze-related parameters of a user is shown. In fact, with the help of FIGS. 1A and 1C a plurality of embodiments shall be represented, wherein said embodiments mainly differ from each other in the position of the cameras 14, 24. Thus, the spectacles device 1 is depicted in FIG. 1A with more than one camera 14, 24 per ocular opening 11, 21 only for presenting each embodiment. However, in this embodiment the spectacles device does not comprise more than one camera 14, 24 associated to each ocular opening 11, 21.

FIG. 1A is a view from above on said spectacles device 1, wherein the left side 10 of the spectacles device 1 is shown on the right side of the drawing sheet of FIG. 1A and the right side 20 of the spectacles device 1 is depicted on the left side of the drawing sheet of FIG. 1A. The spectacles device 1 has a middle plane 100, which coincides with a median plane of the user of the spectacles device 1 when worn according to the intended use of the spectacles device 1. With regard to user's intended use of the spectacles device 1, a horizontal direction 101, a vertical direction 102, 100, a direction "up" 104, a direction "down" 103, direction towards the front 105 and a direction towards the back 106 are defined.

The spectacles device 1 as depicted in FIG. 1A, FIG. 1B, and FIG. 1C comprises a spectacles body 2 having a frame 4, a left holder 13 and a right holder 23. Furthermore, the spectacles body 2 delimits a left ocular opening 11 and a right ocular opening 21, which serve the purpose of providing an optical window for the user to look through, similar to a frame or a body of normal glasses. A nose bridge portion 3 of the spectacles body 2 is arranged between the ocular openings 11, 21. With the help of the left and the right holder 13, 23 and support elements of the nose bridge portion 3 the spectacles device 1 can be supported by ears and a nose of the user. In the following, the frame 4 is also referred to as front frame and spectacles frame, respectively.

According to the embodiments represented by FIG. 1A, a left eye camera 14 and/or a right eye camera 24 can be arranged in the spectacles body 2. Generally, the nose bridge portion 3 or a lateral portion 12 and/or 22 of the spectacles body 2 is a preferred location for arranging/integrating a camera 14, 24, in particular a micro-camera.

Different locations of the camera(s) 14, 24 ensuring a good field of view on the respective eye(s) may be chosen. In the following some examples are given.

If a camera 14 or 24 is arranged in the nose bridge portion 3 of the spectacles body 2, the optical axis 15 of the left camera 14 may be inclined with an angle $\alpha$ of 142° to 150°, preferred 144°, measured in counter-clockwise direction (or −30° to −38°, preferred −) 36° with respect to the middle plane 100. Accordingly, the optical axis 25 of the right camera 24 may have an angle $\beta$ of inclination of 30° to 38°, preferred 36°, with respect to the middle plane 100.

If a position of a camera 14, 24 is located in one of the lateral portions 12, 22 of the spectacles body 2, the optical axis 15 of the left camera 14 may have an angle $\gamma$ of 55° to 70°, preferred 62° with respect to the middle plane, and/or the optical axis 25 of the right camera 24 may be inclined about an angle $\delta$ of 125° to 110° (or −55° to)−70°, preferred 118° (or)−62°.

Furthermore, a bounding cuboid 30—in particular a rectangular cuboid—may be defined by the optical openings 11, 21, which serves four specifying positions of camera placement zones 17, 27, 18, 28. As shown in FIG. 1A, FIG. 1B, and FIG. 1C the bounding cuboid 30—represented by a dashed line—may include a volume of both ocular openings 11, 21 and touches the left ocular opening 11 with a left lateral surface 31 from the left side 10, the right ocular opening 21 with a right lateral surface 32 from the right side 20, at least one of the ocular openings 11, 21 with an upper surface 33 from above and from below with a lower surface 34.

In case a left/right camera 14, 24 is arranged in the nose bridge portion 3, a projected position of the left camera 14 would be set in a left inner eye camera placement zone 17 and the right camera 24 would be (projected) in the right inner eye camera placement zone 27.

When being in the left/right lateral portion 12, 22, the left camera 14 may be positioned—when projected in the plane of the camera placement zones—in the left outer eye camera placement zone 18, and the right camera 24 is in the right outer eye camera placement zone 28.

With the help of the front view on the spectacles device 1 depicted in FIG. 1B the positions of the eye camera placement zones 17, 18, 27, 28 are explained. In FIG. 1B rectangular squares represent said eye camera placement zones 17, 18, 27, 28 in a vertical plane perpendicular to the middle plane 100.

As a preferred option, all embodiments of the spectacles device 1 as represented by FIG. 1A to 1C have in common, that no more than one camera 14/24 is associated to one of the optical openings 11, 21. Typically, the spectacles device 1 does only comprise one or two cameras 14, 24 to take a picture of a left and a right eyeball 19, 29, respectively.

The spectacles device 100 as shown in FIG. 1A comprises a computing and control unit 7 configured for processing the left and/or the right picture from the respective camera 14, 24 for determining parameter(s) of the respective eye.

Typically, the computing and control unit is non-visibly integrated within the holder, for example within the right holder 23 or the left holder 13 of the spectacles device 1. According to a non-shown embodiment, a processing unit can be located within the left holder. Alternatively, the processing of the left and the right images from the cameras 14, 24 for determining the gaze-related parameter(s) may alternatively be performed by a connected companion device such as smartphone or tablet or other computing device such as a desktop or laptop computer, and may also be performed entirely offline, based on videos recorded by the left and/or right cameras 14, 24.

The head wearable device 1 may also include components that allow determining the device orientation in 3D space, accelerometers, GPS functionality and the like.

The head wearable device 1 may further include any kind of power source, such as a replaceable or rechargeable battery, or a solar cell. Alternatively (or in addition), the head wearable device may be supplied with electric power during operation by a connected companion device such as smartphone or tablet, and may even be free of a battery or the like.

According to an embodiment, the computation of the user's eye parameter(s) as explained herein is done by computing and control unit 7 which is fully and invisibly integrated into a standard spectacle frame.

The head wearable device may however also be embodied in configurations other than in the form of spectacles, such as for example as integrated in the nose piece or frame assembly of an AR or VR head-mounted display (HMD) or goggles or similar device, or as a separate nose clip add-on or module for use with such devices.

Figure 2B:
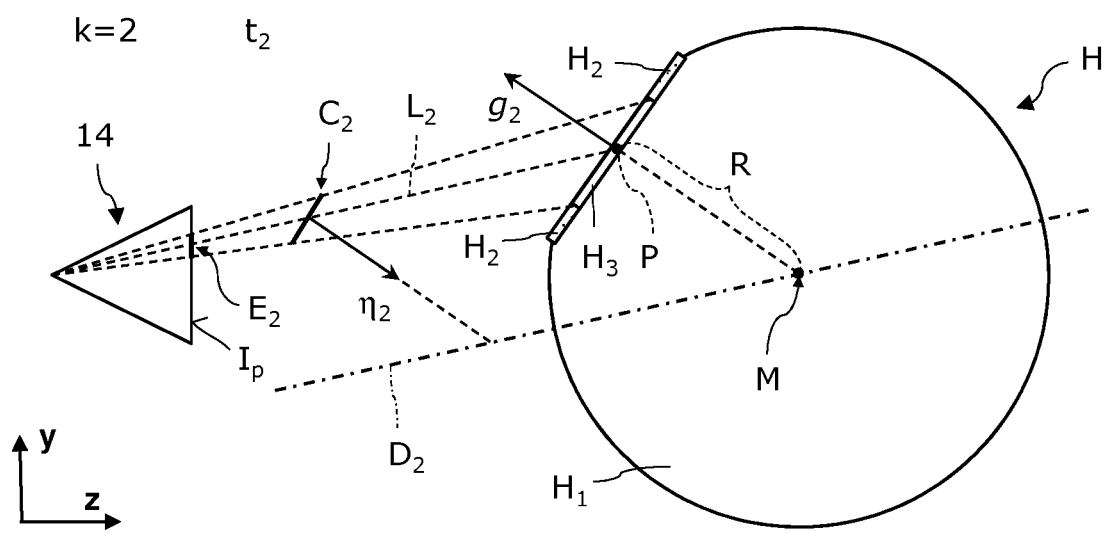
Figure 2C:
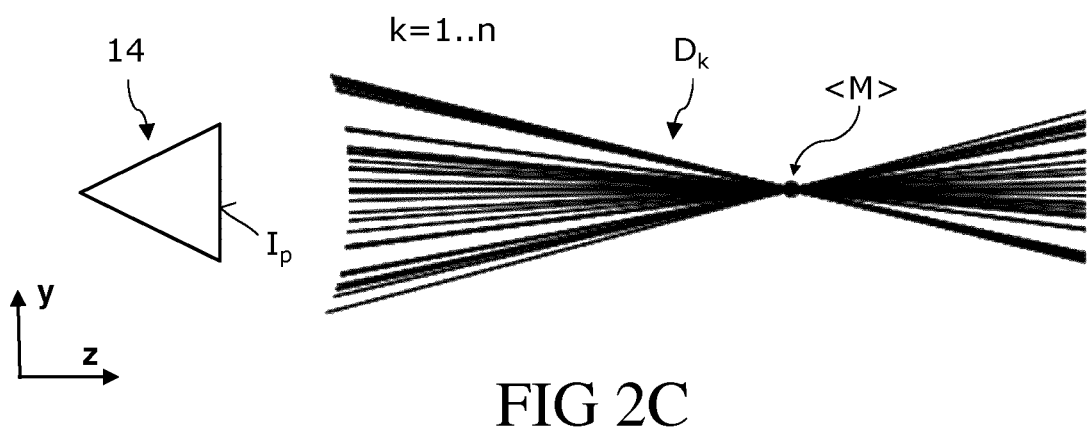

FIG. 2A to 2C illustrates processes of a method for generating data suitable for determining a parameter of a human eye.

With respect to FIG. 2A, 2B illustrating a camera 14 and the human eye H in the field of view of the camera 14, determining of eye intersecting lines $D_1$ and $D_2$ is explained. The camera 14 is typically a near eye camera as explained above with regard to FIGS. 1A to 1C. For the sake of clarity, a Cartesian coordinate system y, z is additionally shown. In the exemplary embodiment, the z-direction is perpendicular to the image plane $I_p$ of the camera 14.

In the exemplary embodiment, the camera 14 used for taking images of the user's eye is modelled as a pinhole camera. The user's eye H is represented by an appropriate model for human eyes. In particular, a two sphere eye model as illustrated in FIG. 3A may be used.

Figure 3A:
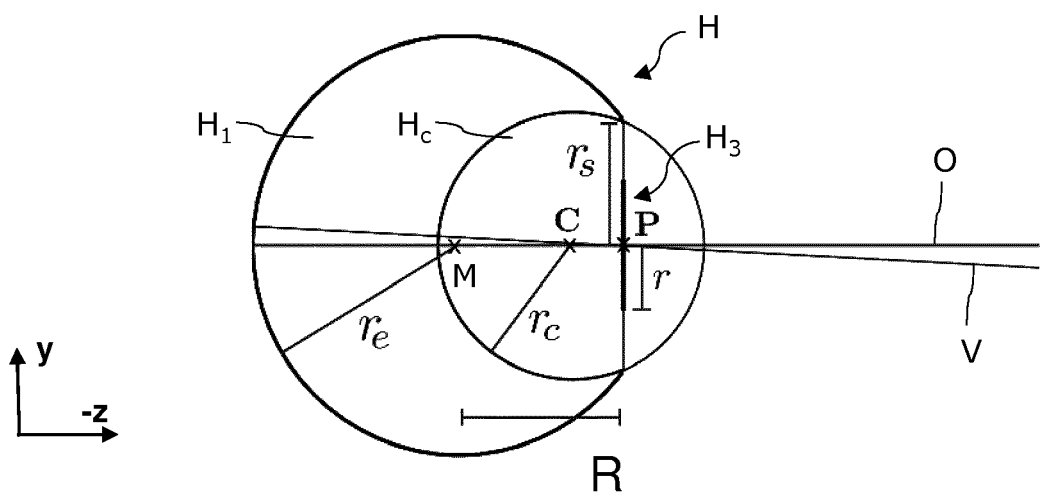
FIG. 3A is a schematic view of an exemplary two-sphere eye model.

FIG. 3A is a schematic view of an exemplary two-sphere model H for human eyes according to LeGrand. It approximates the eye geometry as consisting of two partial spheres. The larger partial sphere $H_1$ corresponds to the eyeball with center at position M=(x, y, z) and radius of curvature $r_e$. The second partial sphere $H_C$ represents the cornea with center C and radius of curvature $r_c$. It is assumed that the cornea and the aqueous humor form a continuous medium with a single effective refractive index, $n_{ref}$. While the effective refractive index of the cornea varies slightly across the human population, it is reasonable to assume it to be fixed to the physiologically plausible value $n_{ref}$=1.3375. The iris and pupil $H_3$ within the LeGrand eye model are two circles with radius $r_s$ and r, respectively, sharing the same center P lying at a distance R=$(r_e^2-r_s^2)^{0.5}$ from M along the direction MC. Their normal directions coincide, are parallel to MC, and thus correspond to the optical axis O of the eye. For calculation the following physiologically plausible values are assumed: radius of curvature $r_e$=12 mm, cornea radius $r_C$=7.8 mm, and iris radius $r_s$=6 mm. The pupil radius typically varies in the physiologically plausible range of approximately 1-4 mm.

Initially, we will focus on estimating the optical axis O of the eye. Depending on the user/person, the optical axis O of the eye may deviate from the visual axis V of the eye H. The state of the model, similar to the one employed by reference [1] (Świrski model), is uniquely determined by specifying the position of the eyeball center M and the pose and radius of the pupil $H_3$=($\phi$, $\theta$, r), where $\phi$ and $\theta$ are the spherical coordinates of the normalized vector pointing from M into the direction of C. We will refer to $\phi$ and $\theta$ as gaze angles. In some cases, we will also refer to the angle between the optical axis O and the negative z-axis as gaze angle.

In reference [1], a complex optimization is performed to estimate eyeball positions as well as gaze angles and pupil size for all observations.

Different thereto, a computationally less demanding two-stage process is proposed herein.

First, the eyeball center M is determined at given times, $t_1$ and $t_2$ in FIGS. 2A, 2B. The other parameters of the eye like gaze-angle and pupil-radius are obtained in a separate step.

In order to determine the eyeball position M, the same disambiguation procedure on pairs of un-projected circles as proposed in reference [1] (see FIG. 3 and corresponding description of [1]) may be used. As a result, we obtain circles $C_1$ and $C_2$ in 3D, corresponding to respective un-projections of outer contours of the pupil $H_3$.

In particular, a first ellipse $E_1$ representing a border (outer contour) of the pupil $H_3$ at the first time $t_1$ is determined in a first image taken with the camera 14. This is typically achieved using image processing techniques.

Likewise, a second ellipse $E_2$ representing the border of the pupil $H_3$ at the second time $t_2$ is determined in a second image taken with the camera 14.

As explained in detail in reference [1] which is incorporated by reference in its entirety, a camera model of the camera 14 is used to determine an orientation vector $\eta_1$ of the first circle $C_1$ and a first center line $L_1$ on which a center of the first circle $C_1$ is located, so that a projection of the first circle $C_1$, in a direction parallel to the first center line $L_1$, onto the image plane $I_p$ reproduces the first ellipse $E_1$ in the image.

Likewise, the camera model may be used to determine an orientation vector $\eta_2$ of the second circle $C_2$ and a second center line $L_2$ on which a center of the second circle $C_2$ is located, so that a projection of the second circle $C_2$, in a direction parallel to the second center line $L_2$, onto the image plane $I_p$ of the camera reproduce the second ellipse $E_2$ in the image.

However, the size-distance ambiguity explained above is resolved in a much simpler manner.

For this purpose, a first eye intersecting line $D_1$ expected to intersect the center M of the eyeball $H_1$ at the first time $t_1$ may be determined as a line which is, in the direction of the orientation vector $\eta_1$, parallel-shifted to the first center line $L_1$ by the expected distance R between the center M of the eyeball $H_1$ and the center P of the pupil $H_3$. As already explained above, the distance R may be set to its average human (physiological) value R=10.39 mm, which is in the following also referred to as a physiological constant of human eyes.

Likewise, a second eye intersecting line $D_2$ expected to intersect the center M of the eyeball $H_1$ at the second time $t_2$ may be determined as a line which is, in the direction of the orientation vector $\eta_2$, parallel-shifted to the second center line $L_2$ by the distance R.

Note that each un-projection circle $C_k$ constrains the eyeball position M in 3D to the respective line $D_k$ (k=1 . . . 2 in FIG. 2A, 2B).

To this end, note that for each choice of pupil radius r, the circle $C_k$ constitutes a 3D pupil candidate that is consistent with the observed pupil ellipse $E_k$. In the framework of the two-sphere model, if the circle $C_k$ were to be the actual pupil, it would thus need to be tangent to a sphere of radius R and position given by $$D_k(r) = c_k^r + R * \eta_k$$

defining a line in 3D that is parameterized by r, in which $c_k^r$ represents the ensemble of possible pupil circle centers, i.e. the circle center line $L_k$.

As the 3D pupil corresponds to $C_k(r)$ when r is chosen to be the actual pupil radius, the eyeball center M thus indeed needs to be contained in this line $D_k$.

Therefore, the center M of the eyeball $H_1$ may be determined as intersection point of the first eye intersecting line $D_1$ and the second eye intersecting line $D_2$ or as nearest point to the first eye intersecting line $D_1$ and the second eye intersecting line $D_2$.

Typically, the eye intersecting lines $D_k$ may be determined for a plurality of different times $t_k$ with k=1 ... n. Each of the eye intersecting lines $D_k$ is expected to intersect the center M of the eyeball at respective times.

Furthermore, the center M of the eyeball is typically determined as nearest point <M> to the eye intersecting lines $D_k$, k=1 ... n (see FIG. 2C). In other words, the center M of the eyeball intersection is in practice typically taken in a least-squares sense.

After determining the eyeball position M, gaze directions $g_1$, $g_2$ may be determined as being negative to the respective orientation vector $\eta_1$, $\eta_2$.

Further, the respective optical axis may be determined as by (normalized) direction from P to the intersection point M.

Figure 3B:
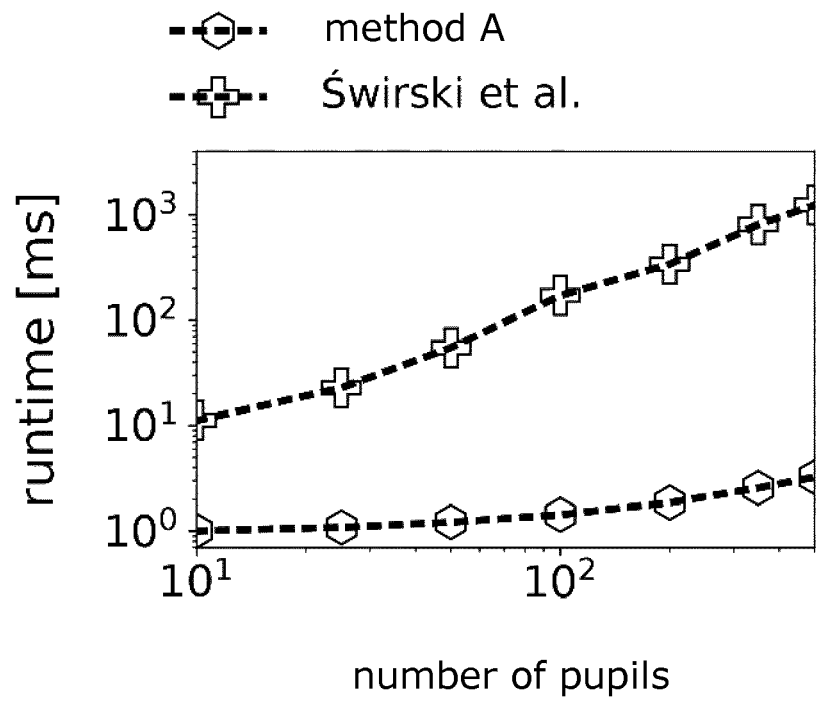
FIG. 3B illustrates the computational runtime of methods for determining a parameter of a human eye.

As illustrated in FIG. 3B, the number of pupils (image frames) that can be calculated with the method explained above with regard to FIGS. 2A to 2C (method A) is, for the same computing hardware, typically at least one order of magnitude higher compared to the method of Swirski (reference [1]).

In other words, the method A as explained herein is at least one order of magnitude more efficient.

FIG. 4A illustrates a flow chart of a method 1000 for generating data suitable for determining a parameter of a human eye according to embodiments. As indicated by the dashed rectangle A, the method 1000 may at least substantially correspond to the method A explained above with regard to FIGS. 2A to 2C.

In a first step 1100, an image $I_k$ of the user's eye may be taken by a near-eye camera of a head-wearable device at a time $t_k$.

In a subsequent step 1200, an ellipse $E_k$ representing a border of the eye's pupil at the time $t_k$ may be determined.

In a subsequent step 1300, a camera model describing the camera of the head wearable device is used to determine an orientation vector of a circle $C_k$ and a center line $L_k$ on which a center of the circle $C_k$ is located, so that a projection of the circle $C_k$, in a direction parallel to the first center line $L_k$, onto an image plane of the camera reproduces the ellipse $E_k$.

Thereafter, the center line $L_k$ may be parallel-shifted by an expected distance between the center of the eyeball and a center of the pupil in the direction of the orientation vector to determine an eye intersecting line $D_k$ which intersects a center M of the user's eyeball at the time $t_k$ in step 1400.

As indicated by the right dashed arrow in FIG. 4A, the index k may be incremented and a new cycle 1100 to 1400 of determining eye intersecting line $D_k$ may be started.

Thereafter, the center M of the eyeball may be determined as (least square) intersection point of the eye intersecting lines $D_k$, with k=1 ... n, in step 1500.

As indicated by the left dashed arrow in FIG. 4A, the procedure may be repeated at a later time again, for example after slippage of the head-wearable device is detected or expected to have happened.

Further, other parameter(s) of the user's eye such as gaze direction and pupil size may be determined when the centre M of the eyeball is known.

Furthermore, the other parameter(s) of the user's eye may also be determined for later times without recalculating the center M (to save computational time).

However, when the determined other parameter(s) of the user's eye exhibit an abnormality, recalculating the center M may be initiated.

Alternatively and/or in addition, a corrected value for the centre M of the eyeball $M_{corr}$ and/or any other parameters of the user's eye determined in/after step 1500 may be determined using a correction function $R_{corr}$ in a subsequent step 1600.

As indicated by the dashed rectangle B, the method 1000 including step 1600 is in the following also referred to as method B.

FIG. 4B illustrates a flow chart of a method 2000 for determining the correction function $R_{corr}$.

In a first step 2100, synthetic camera images $SI_1$ of several model eyeballs of the human eye (H) with varying effective corneal refraction index $n_{ref}$ and a plurality of given values $\{X_{gt}\}$ of one or more (geometric) parameters $\{X\}$ of the model eyeball are determined using a model of the camera such as a pinhole model. For example, a ray tracer may be used to generate the synthetic camera images. For accuracy reasons, synthetic images may be ray traced at arbitrarily large image resolutions.

In step 2200, the synthetic camera images St are used to determine expected values of the one or more parameters $\{X_{ex}\}$. As explained below in more detail with regard to FIG. 4C, the expected values of the one or more parameters $\{X_{ex}\}$ are typically determined in analogy to method 1000 used to determine the one or more parameters of a human eye, but based on the synthetic camera images SI'.

Thereafter, the correction function $R_{corr}$:

$$R_{corr}(\{X_{ex}\}, n_{ref}) = \{X_{gt}\}$$

mapping, depending on the effective corneal refraction index $n_{ref}$ (independent parameter), the expected values $\{X_{ex}\}$ to the respective given (ground truth) values $\{X_{gt}\}$ may be determined in a step 2300.

This is typically achieved by a (multivariate) polynomial regression analysis.

As indicated by the dashed-dotted arrow in FIGS. 4A, 4B, the correction function $R_{corr}$ may be used to correct the parameters determined by method A (for example $M_{corr}=R_{corr}(M)$).

The correction function $R_{corr}$ may be determined in two stages. In a first stage, a correction function $R_{eye}$ for the eyeball center M obeying $$R_{eye}(M_{ex}, n_{ref}) = M_{gt} \quad (1)$$

with the effective corneal refraction index $n_{ref}$ as independent parameter to be able to account for variations in the effective refractive index of the cornea across subjects may be determined. In the equation (1) $M_{gt}$ and $M_{ex}$ refer to the eyeball position set for generating the synthetic camera images and the (expected) eyeball position determined from the synthetic camera images, respectively.

Note that due to the nonlinear nature of corneal refraction, the derivation of an exact closed-form representation of $R_{eye}$ is challenging. However, $R_{eye}$ may be estimated by an empirical correction function in the following manner.

After fixing $M_{gt}$ at a position randomly drawn from a range of practically relevant eyeball positions, here x,y∈[−5, 5] and z∈[25, 45], we generated 25 synthetic eye images for each fixed value of $n_{ref}$ randomly drawn from [1.1, 1.4], with gaze angles ϕ and θ randomly chosen from a uniform distribution between −50° and 50°, and with pupil radii randomly chosen from a uniform distribution between 1 mm and 4 mm. Pupil contours were extracted from all images using Pupil Capture, the open source software developed by Pupil Labs (see e.g. reference [3]). Based on the extracted contours, we obtained an eyeball position estimate $M_{ex}$ as explained below with regard to FIG. 4C. Typically, a large number N of parameter tuples $\{M_{ex}^i, n_{ref}^i\} \leftrightarrow \{M_{gt}^i\}$ with i:=1 . . . N maybe determined this way and used to estimate $R_{eye}$ in a least-squares sense by means of a multivariate polynomial regression. For example, N maybe 1000 and the degree of the polynomial regression may be five.

Thereafter, a correction function $R_{pupil}$, which may be used to correct gaze-angles and pupil-radius and obeys $$R_{pupil}(\vec{g}_{ex}, r_{ex}, M, n_{ref}) = (\vec{g}_{gt}, r_{gt}) \quad (2)$$

with fixed eyeball centre M, (ground truth) gaze vector $\vec{g}_{gt}$ set for generating the synthetic camera images, (expected) gaze vector $\vec{g}_{ex}$ determined from the synthetic camera images, (ground truth) pupil radius $r_{gt}$ set for generating the synthetic camera images, and (expected) pupil radius $r_{ex}$ determined from the synthetic camera images.

Similar as explained for correction function $R_{eye}$, synthetic eye images may be determined for gaze vectors corresponding to gaze angles ϕ and θ evenly spanning a field of view of e.g. −50° and 50°, and pupil radii randomly chosen from a uniform distribution between 1 mm and 4 mm, and analysed as explained below with regard to FIG. 4C.

The resulting parameter tuples $\{\vec{g}_{ex}, r_{ex}, M, n_{ref}\} \leftrightarrow \{\vec{g}_{gt}, r_{gt}\}$ may be used to estimate $R_{pupil}$ in a least-squares sense by means of a multivariate polynomial regression.

FIG. 4C illustrates a flow chart of step 2200 of the method 2000 explained above with regard to FIG. 4B.

In a first step 2220, in each synthetic camera image $SI_1$ a respective ellipse $E_1$ at least substantially representing a border of the pupil (of the model eye used for generating the synthetic camera images $SI_1$) is determined.

Thereafter, respective orientation vectors $\eta_1$ of circles $C_1$ and center lines $L_1$ on which a center of the respective circle $C_1$ is located are determined in step 2230 using the camera model used for generating the synthetic camera images $SI_1$, so that a projection of the circle $C_1$, in a direction parallel to the first center line $L_1$, onto the image plane of the camera model reproduces the respective ellipse $E_1$.

Thereafter, respective eye intersecting lines $D_1$ expected to intersect a center of the eyeball may be determined in step 2240 as lines which are, in the direction of the respective orientation vector $\eta_1$, parallel-shifted to the respective center line $L_1$ by the expected distance R between the center of the eyeball and the center of the pupil (of the model eye).

Thereafter, the eye intersecting lines $D_1$ may be used to determine the expected values of the eyeball center $M_{ex}$ (typically as least square intersecting point) as a parameter $X_{ex}$. Based on $M_{ex}$ other expected parameter values $\{X_{ex}\}$ may be determined.

Alternatively, the correction function $R_{corr}$ may be calculated as a single correction function in one stage only, such that $$R_{corr}(\vec{g}_{ex}, r_{ex}, M_{ex}, n_{ref}) = (\vec{g}, r, M)$$

Figure 5A:
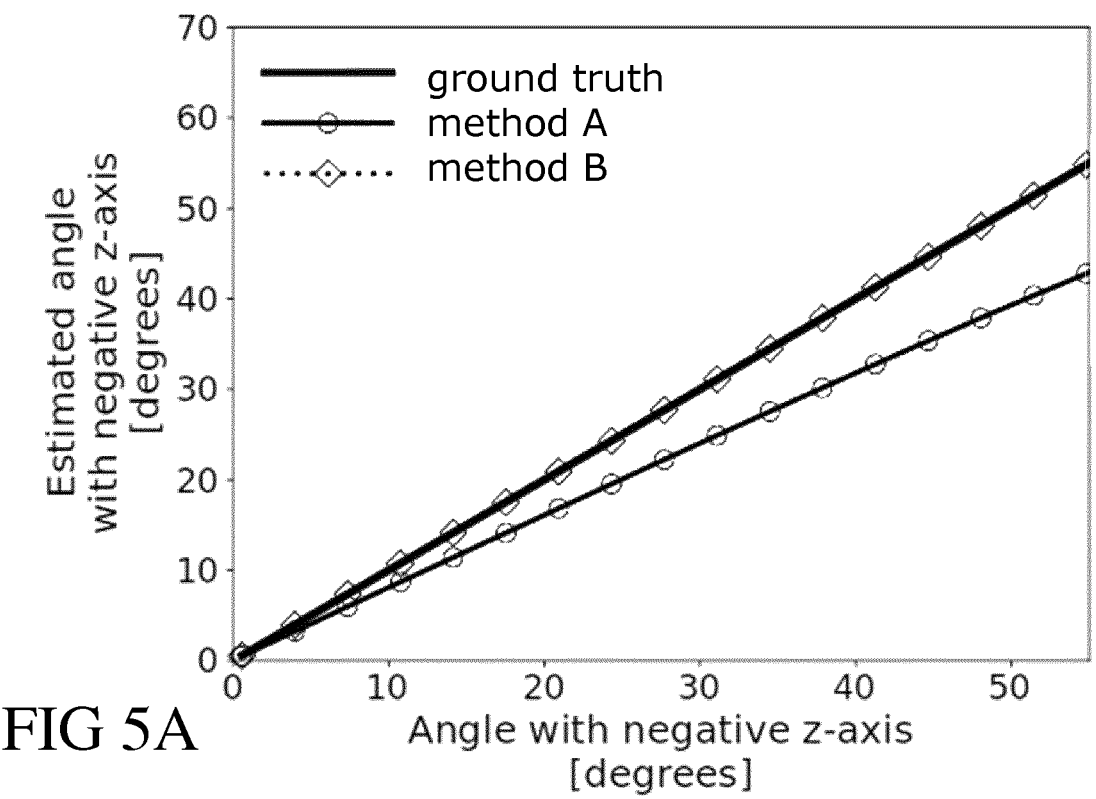
FIG. 5A shows curves for estimated gaze angles of the optical axis as a function of the respective ground truth value.
Figure 5B:
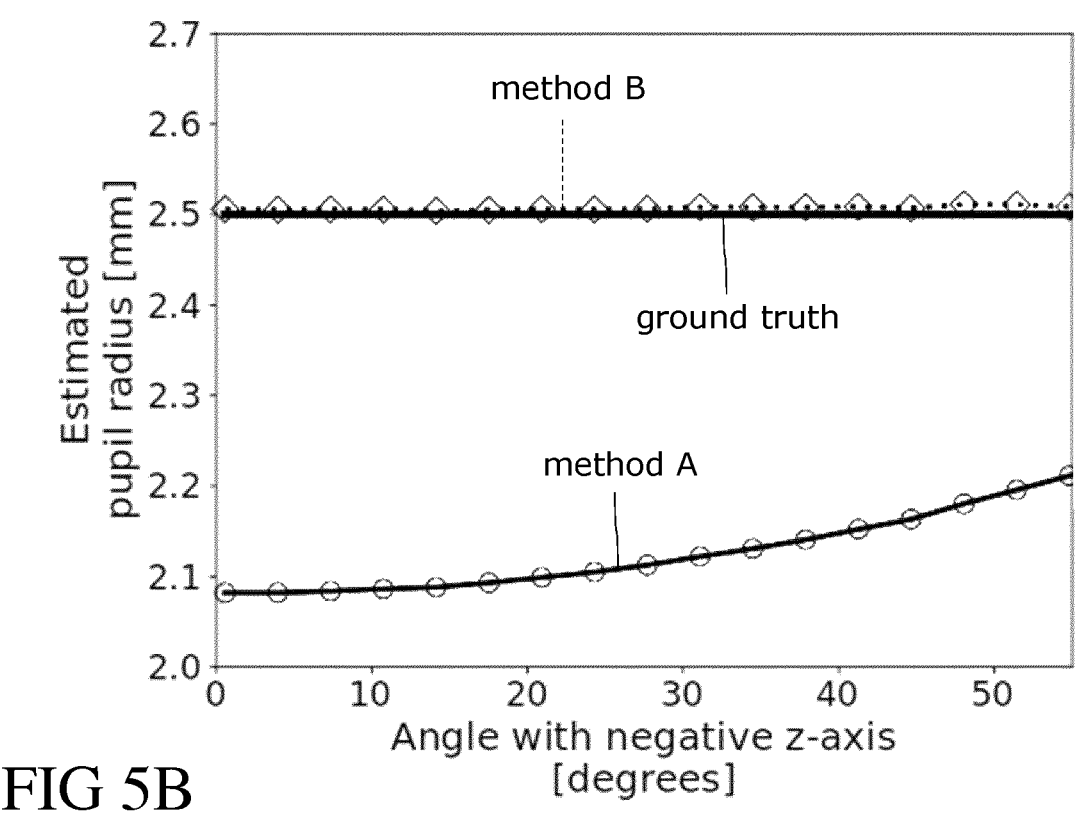
FIG. 5B shows curves for estimated pupil radius as a function of ground truth value of the angle of the optical axis.

The accuracy of gaze-angle and pupil-radius estimated (obtained) with the methods A (without using the correction function) and B (using the correction function) explained above with regard to FIG. 4A to 4C is illustrated in FIGS. 5A, 5B, respectively. In both figures, estimates are shown as a function of the respective ground truth gaze angle value. As can be seen, method B reproduces the ground truth value with high accuracy. Note that an accuracy of better than 1° can be achieved. Different thereto, method A which does not take into account corneal refraction effects underestimates the pupil radius and the gaze angle.

Figure 6A:
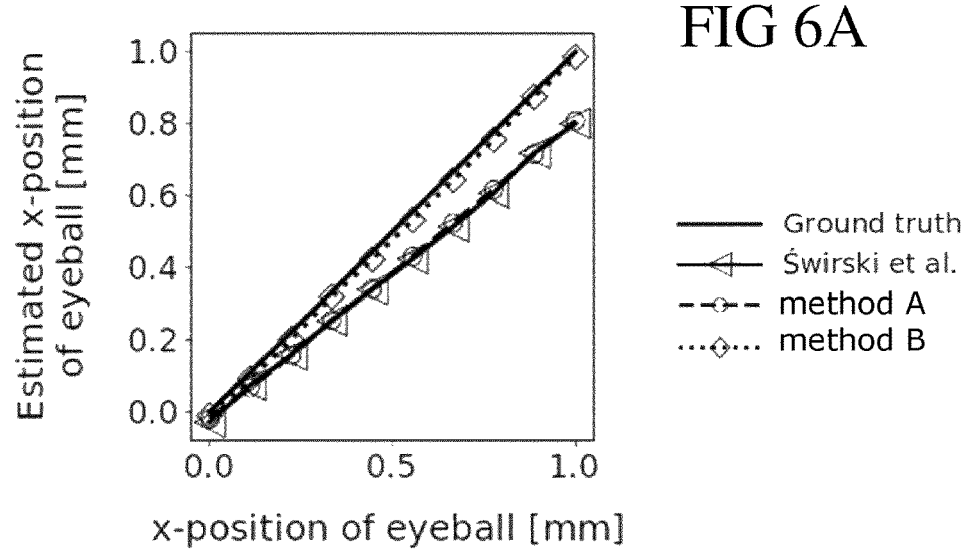
FIG. 6A to 6C show curves for the estimated eyeball position as a function of the respective ground truth value.
Figure 6B:
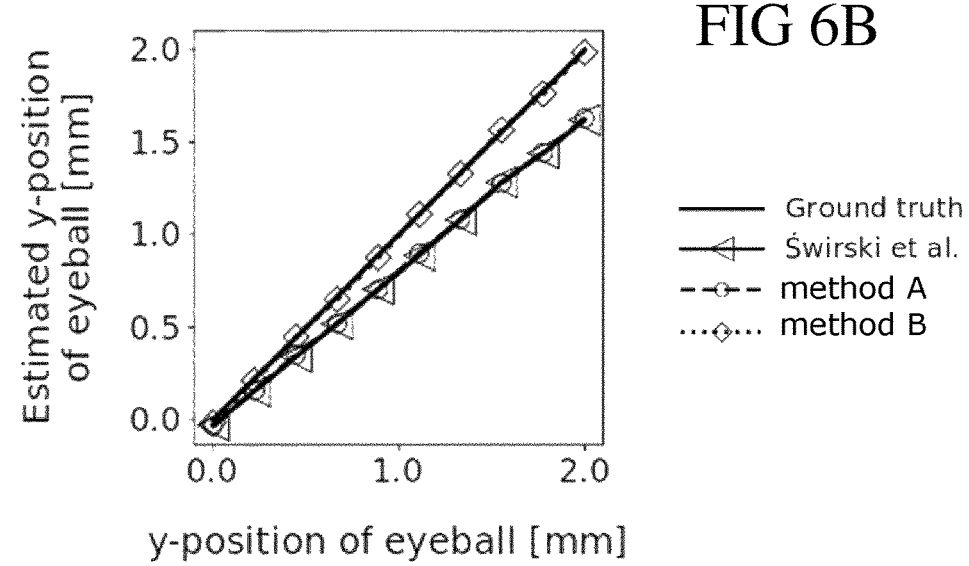
Figure 6C:
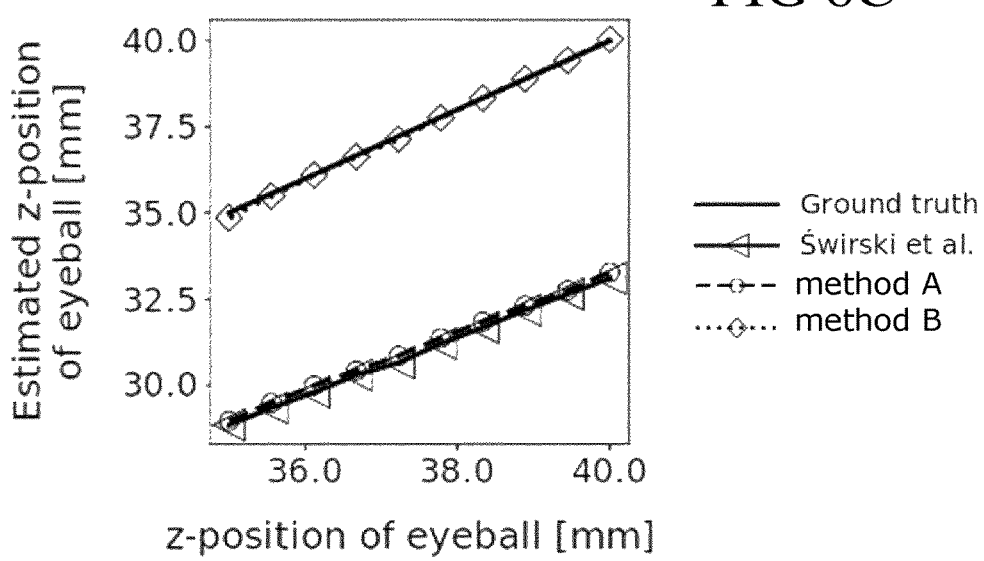

As can be seen in FIG. 6A to FIG. 6C showing curves for the estimated x-, y-, and z-values of eyeball position as function of the respective ground truth value, method B (using the correction function) accurately reproduces the ground truth value of the eyeball coordinates while method A and the method explained in reference [1] (Swirski et al.) deviate systematically from the ground truth values. While the accuracy of method A and the method of Swirski et al. is comparable, the computational effort for method A is at least one order of magnitude lower (see also FIG. 3B).

Despite the systematic error, method A may be used for quantitative studies, e.g. for determining relative changes of eye parameters.

According to the present disclosure, a method for generating data suitable for determining a parameter of a human eye is provided, which opens the way to a fast non-iterative approach to refraction-aware 3D eye-model fitting and gaze prediction based on pupil contours alone. Leveraging geometrical insights with regard to the LeGrand two-sphere eye model, the task of eyeball-position estimation is cast as a (least-squares) intersection of lines. Systematic errors due to corneal refraction may be accounted both in eyeball-position and gaze and pupil-radius estimation by means of empirical correction function(s). This approach provides at comparatively low computational costs accurate estimates for eyeball position, gaze angle, and pupil radius, even in the presence of pupil contour noise (not shown data of a statistical analysis of results obtained for real eye images).

One assumption made is that the eyeball centre is (substantially) stationary in the camera coordinate system. So-called head-set slippage, i.e. unavoidable movements of the headset with respect to the head of the user, may render this assumption only approximately true. Note that headset slippage can occur on timescales as short as minutes and may therefore constitute a challenge for head-mounted eye-tracking solutions. A promising route for mitigating the deteriorating effect of headset slippage is the continuous real-time update of eyeball position over the course of a recording similar as explained above with regard to FIG. 4A. Earlier formulations of the eye-model optimization procedure, as e.g. presented in reference [1], involve time-intensive iterative solving of a non-linear minimization problem. Different thereto, the methods explained herein provide a fast non-iterative solution. Accordingly, the computational complexity and cost are considerably reduced. This also opens possibilities for devising more refined algorithms for detecting and correcting headset slippage. For example, a statistical analysis of eyeball-position estimates obtained from subsets of the most recent eye images may be used to deduce insights into the current slippage-paradigm and inform strategies for when to perform real-time eye model updates and which data from the most recent past to use.

According to an embodiment of a method for generating data suitable for determining a parameter of an eye, in particular a geometric parameter of the eye such as the center of the eyeball of the eye, a radius of a pupil of the eye, a size of the pupil and a gaze-direction related parameter of the eye, the method includes: receiving a first image of the eye, the first image being taken at a first time with a camera, typically a near-eye camera, more typically a near-eye camera of a head-wearable device as described herein, determining a first ellipse in the first image, the first ellipse at least substantially representing a border of the pupil at the first time, using a camera model, typically a pinhole camera model, describing the camera defining an image plane, to determine an orientation vector of a first circle and a first center line on which a center of the first circle is located, so that a projection of the first circle, in a direction parallel to the first center line, onto the image plane reproduces the first ellipse, and determining a line which is, in the direction of the orientation vector, parallel-shifted to the first center line by an expected distance between a center of an eyeball of the eye and a center of a pupil of the eye as a first eye intersecting line which intersects the center of the eyeball at the first time.

According to an embodiment of a method for generating data for determining a correction function for a parameter of an eye which is derivable from at least one image of the eye taken with a camera of known imaging characteristics that may be defined by camera intrinsics, in particular a geometric parameter of the eye such as the center of the eyeball of the eye, a radius of a pupil of the eye, a size of the pupil and a gaze-direction related parameter of the eye, the method includes using the known imaging characteristics to generate synthetic camera images of several model eyeballs of the eye with varying effective corneal refraction index of the eye and for a plurality of given values of the parameter of the model eyeballs. The synthetic camera images are used to determine expected values of the parameter. The expected values of the parameter and the given values of the parameter are used to determine a correction function which maps, depending on the effective corneal refraction index, the expected values of the parameter to the respective given values of the parameter.

Although various exemplary embodiments of the invention have been disclosed, it will be apparent to those skilled in the art that various changes and modifications can be made which will achieve some of the advantages of the invention without departing from the spirit and scope of the invention. It will be obvious to those reasonably skilled in the art that other components performing the same functions may be suitably substituted. It should be mentioned that features explained with reference to a specific figure may be combined with features of other figures, even in those cases in which this has not explicitly been mentioned. Such modifications to the inventive concept are intended to be covered by the appended claims.

While processes may be depicted in the figures in a particular order, this should not be understood as requiring, if not stated otherwise, that such operations have to be performed in the particular order shown or in sequential order to achieve the desirable results. In certain circumstances, multitasking and/or parallel processing may be advantageous.

Spatially relative terms such as "under", "below", "lower", "over", "upper" and the like are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc. and are also not intended to be limiting Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

With the above range of variations and applications in mind, it should be understood that the present invention is not limited by the foregoing description, nor is it limited by the accompanying drawings. Instead, the present invention is limited only by the following claims and their legal equivalents.

REFERENCES

[1] L. Swirski and N. Dodgson: "*A fully-automatic, temporal approach to single camera, glint free* 3*D eye model fitting*", Proc. PETMEI Lund/Sweden, 13 Aug. 2013

[2] R. Navarro, J. Santamaría, J. Bescós: "Accommodation-dependent model of the human eye with aspherics," J. Opt. Soc. Am. A 2(8), 1273-1281 (1985)

[2] M. Kassner, W. Patera, and A. Bulling. 2014. Pupil: an Open Source Platform for Pervasive Eye Tracking and Mobile Gaze-Based Interaction. In Proceedings of the 2014 ACM International Joint Conference on Pervasive and Ubiquitous Computing: Adjunct Publication. ACM, 1151-1160

REFERENCE NUMBERS 1 head wearable device, head wearable spectacles device
2 main body, spectacles body
3 nose bridge portion
4 frame
5 illumination means
6
7 computing and control unit
8
9
10 left side
11 left ocular opening
12 left lateral portion
13 left holder/left temple (arm)
14 left camera
15 optical axis (left camera)
16
17 left inner eye camera placement zone 18 left outer eye camera placement zone
19 left eye
20 right side
21 right ocular opening
22 right lateral portion
23 right holder/right temple (arm)
24 right camera
25 optical axis (right camera)
26
27 right inner eye camera placement zone
28 left outer eye camera placement zone
29 right eye
30 bounding cuboid
31 left lateral surface
32 right lateral surface
33 upper surface
34 lower surface
100 middle plane
101 horizontal direction
102 vertical direction
103 down
104 up
105 front
106 back
α angle of inner left camera 14
β angle of inner right camera 24
γ angle of outer left camera 14
δ angle of outer right camera 24
>=1000 methods, method steps

The invention claimed is:

1. A method for generating data suitable for determining a parameter of a human eye comprising an eyeball and an iris defining a pupil, the method comprising:
   receiving a first image of the eye for a first time from a camera of known camera intrinsic s and defining an image plane;
   determining a first ellipse in the first image, the first ellipse at least substantially representing a border of the pupil at the first time;
   using the camera intrinsics and the first ellipse to determine an orientation vector of a first circle and a first center line on which a center of the first circle is located, so that a projection of the first circle, in a direction parallel to the first center line, onto the image plane is expected to reproduce the first ellipse;
   determining a first eye intersecting line expected to intersect a center of the eyeball at the first time as a line which is, in the direction of the orientation vector, parallel-shifted to the first center line by an expected distance between the center of the eyeball and a center of the pupil; and
   wherein the expected distance between the center of the eyeball and the center of the pupil is an average value, in particular a physiological constant, wherein the orientation vector points away from the camera, wherein the camera de fines a co-ordinate system, wherein at least the respective center lines are determined with respect to the co-ordinate system, wherein the camera is assumed to be substantially immobile with respect to the eye, and/or wherein the center of the eyeball is assumed to have at least substantially non-varying co-ordinates in the co-ordinate system while the respective images of the eye are acquired by the camera.

2. The method of claim 1, further comprising:
   receiving a second image of the eye for a second time from the camera;
   determining a second ellipse in the second image, the second ellipse at least substantially representing the border of the pupil at the second time;
   using the camera intrinsics and the second ellipse to determine an orientation vector of a second circle and a second center line on which a center of the second circle is located, so that a projection of the second circle, in a direction parallel to the second center line, onto the image plane is expected to reproduce the second ellipse; and
   determine a second eye intersecting line expected to intersect the center of the eyeball at the second time as a line which is, in the direction of the orientation vector of the second circle, parallel-shifted to the second center line by the expected distance.

3. The method of claim 2, further comprising using the first eye intersecting line and the second eye intersecting line to determine expected co-ordinates of the center of the eyeball.

4. The method of claim 1, further comprising determining for at least one of the times an expected gaze direction of the eye as a vector which is antiparallel to the respective orientation vector.

5. The method of claim 1, wherein the method does not take into account a glint from the eye for generating data suitable for determining the parameter of the human eye, wherein the method is glint-free, and/or wherein the method does not use structured light and/or special purpose illumination to derive parameters of the eye.

6. A method for generating data suitable for determining a parameter of a human eye comprising an eyeball and an iris defining a pupil, the method comprising:
   receiving a first image of the eye for a first time from a camera of known camera intrinsics and defining an image plane;
   determining a first ellipse in the first image, the first ellipse at least substantially representing a border of the pupil at the first time;
   using the camera intrinsics and the first ellipse to determine an orientation vector of a first circle and a first center line on which a center of the first circle is located, so that a projection of the first circle, in a direction parallel to the first centerline, onto the image plane is expected to reproduce the first ellipse;
   determining a first eye intersecting line expected to intersect a center of the eyeball at the first time as a line which is, in the direction of the orientation vector, parallel-shifted to the first center line by an expected distance between the center of the eyeball and a center of the pupil;
   receiving a second image of the eye fora second time from the camera;
   determining a second ellipse in the second image, the second ellipse at least substantially representing the border of the pupil at the second time;
   using the camera intrinsics and the second ellipse to determine an orientation vector of a second circle and a second center line on which a center of the second circle is located, so that a projection of the second circle, in a direction parallel to the second centerline, onto the image plane is expected to reproduce the second ellipse;
   determine a second eye intersecting line expected to intersect the center of the eyeball at the second time as a line which is, in the direction of the orientation vector of the second circle, parallel-shifted to the second centerline by the expected distance;

further comprising using the first eye intersecting line and the second eye intersecting line to determine expected co-ordinates of the center of the eyeball; and wherein the center of the eyeball is determined as intersection point of the first eye intersecting line and the second eye intersecting line or as nearest point to the first eye intersecting line and the second eye intersecting line, in particular as a least square intersection point of the first eye intersecting line and the second eye intersecting line, wherein the center of the eyeball is at least one of a center of rotation of the eyeball and an optical center of the eyeball, wherein the center of the eyeball is determined using a plurality of eye intersecting lines each of which is expected to intersect the center of the eyeball at respective times, where n is greater than or equal to 2, wherein the center of the eyeball is determined as nearest point to the plurality of eye intersecting lines, and/or wherein the respective images which are used to determine the plurality of eye intersecting lines are acquired with a frame rate of at least 30 frames per second.

7. A method for generating data suitable for determining a parameter of a human eye comprising an eyeball and an iris defining a pupil, the method comprising:
receiving a first image of the eye for a first time from a camera of known camera intrinsics and defining an image plane;
determining a first ellipse in the first image, the first ellipse at least substantially representing a border of the pupil at the first time;
using the camera intrinsics and the first ellipse to determine an orientation vector of a first circle and a first center line on which a center of the first circle is located, so that a projection of the first circle, in a direction parallel to the first centerline, onto the image plane is expected to reproduce the first ellipse;
determining a first eye intersecting line expected to intersect a center of the eyeball at the first time as a line which is, in the direction of the orientation vector, parallel-shifted to the first center line by an expected distance between the center of the eyeball and a center of the pupil;
receiving a second image of the eye for a second time from the camera;
determining a second ellipse in the second image, the second ellipse at least substantially representing the border of the pupil at the second time;
using the camera intrinsics and the second ellipse to determine an orientation vector of a second circle and a second center line on which a center of the second circle is located, so that a projection of the second circle, in a direction parallel to the second center line, onto the image plane is expected to reproduce the second ellipse;
determine a second eye intersecting line expected to intersect the center of the eyeball at the second time as a line which is, in the direction of the orientation vector of the second circle, parallel-shined to the second centerline by the expected distance;
further comprising using the first eye intersecting line and the second eye intersecting line to determine expected co-ordinates of the center of the eyeball; and
further comprising using the expected co-ordinates of the center of the eyeball to determine for at least one of the times at least one of an expected optical axis of the eye, an expected orientation of the eye, an expected visual axis of the eye, an expected size of the pupil and/or an expected radius of the pupil, and/or to determine for a later time, using a later image of the eye acquired at the later time at least one of an expected optical axis of the eye, an expected orientation of the eye and an expected visual axis of the eye, an expected size of the pupil and/or an expected radius of the pupil.

8. A method for determining a correction function for at least one parameter of a human eye, the at least one parameter being derivable from at least one image of the human eye taken with a camera of known camera intrinsics, the method comprising:
calculating, using the known camera intrinsics, synthetic camera images of several model eyeballs of the human eye with varying effective corneal refraction index, for a plurality of given values of the at least one parameter of the model eyeballs;
using the synthetic camera images to determine expected values of the at least one parameter;
using the expected values of the at least one parameter and the given values of the at least one parameter to determine a correction function mapping, depending on the effective corneal refraction index, the expected values of the at least one parameter to the respective given values of the at least one parameter; and
wherein the given values comprise at least one of co-ordinates of respective centers of the model eyeballs, given radii of a pupil of the model eyeballs, and given gaze directions of the model eyeballs, wherein determining the expected values comprises determining respective eye intersecting lines expected to intersect the center of the respective model eyeball for the at least one parameter, the plurality of given co-ordinates of respective center; of the model eyeballs, given radii of a pupil of the model eyeballs and/or given gaze directions, wherein determining the correction function comprises a multivariate polynomial regression analysis, and/or wherein calculating the synthetic camera images comprises raytracing an arrangement of a camera model describing the camera and the model e ye balls arranged in the field of view of the camera model, and/or where in two-sphere eye models are used as model of the eye.

9. The method of claim 8, further comprising using the correction function to correct the parameter of a human eye and/or to determine a corrected value for at least one of the center of the eyeball of the human eye, the expected gaze direction of the human eye, the expected optical axis of the human eye, the expected orientation of the human eye, the expected visual axis of the human eye, the expected size of the pupil of the human eye and the expected radius of the pupil of the human eye.

10. A method for determining a correction function for at least one parameter of a human eye, the at least one parameter being derivable from at least one image of the human eye taken with a camera of known camera intrinsics, the method comprising:
calculating, using the known camera intrinsics, synthetic camera images of several model eyeballs of the human eye with varying effective corneal refraction index, for a plurality of given values of the at least one parameter of the model eyeballs;
using the synthetic camera images to determine expected values of the at least one parameter;
using the expected values of the at least one parameter and the given values of the at least one parameter to determine a correction function mapping, depending on the effective corneal refraction index, the expected values of the at least one parameter to the respective given values of the at least one parameter; and wherein the respective center line and/or the respective eye intersecting line is determined using a model of the camera and/or a three-dimensional eye model, wherein the three-dimensional eye model is a two-sphere eye model, wherein the camera is modelled as a pinhole camera, and/or wherein the model of the camera comprises at least one of a focal length, a shift of a central image pixel, a shear parameter, and a distortion parameter, wherein the camera defines a co-ordinate system, wherein at least the respective center lines are determined with respect to the co-ordinate system, wherein the camera is assumed to be substantially immobile with respect to the eye, and/or wherein the center of the eyeball is assumed to have at least substantially non-varying co-ordinates in the co-ordinate system while the respective images of the eye are acquired by the camera.

11. A system for generating data suitable for determining a parameter of a human eye, the system comprising:
a head-wearable device comprising a camera of known camera intrinsics for taking images of an eye of a user wearing the head-wearable device, the camera comprising a sensor defining an image plane, the eye comprising an eyeball and an iris defining a pupil; and
a computing and control unit configured to:
receive from the camera a first image of the eye of the user taken at a first time;
determine a first ellipse in the first image, the first ellipse at least substantially representing a border of the pupil at the first time;
use the camera intrinsics and the first ellipse to determine an orientation vector of a first circle and a first center line on which a center of the first circle is located, so that a projection of the first circle, in a direction parallel to the first center line, onto the image plane is expected to reproduce the first ellipse;
determine a first eye intersecting line expected to intersect a center of the eyeball at the first time as a line which is, in the direction of the orientation vector, parallel-shifted to the first center line by an expected distance between the center of the eyeball and a center of the pupil; and
wherein the head-wearable device comprises a further eye camera of known camera intrinsics for taking images of a further eye of the user, the further camera comprising a sensor defining a further image plane of the further camera, the further eye comprising a further eyeball and a further iris defining a further pupil, and wherein the computing and control unit is configured to:
receive from the further camera an image of the further eye of a user taken at a further time;
determine an ellipse in the image, the ellipse at least substantially representing a border of the further pupil at the further time;
use the camera intrinsics and the ellipse to determine an orientation vector of a circle and a center line on which a center of the circle is located, so that a projection of the circle, in a direction parallel to the centerline, onto the further image plane is expected to reproduce the ellipse; and
determine an eye intersecting line expected to intersect a center of the further eyeball at the further time as a line which is, in the direction of the orientation vector of the circle, parallel-shifted to the center line by an expected distance between the center of the further eyeball and a center of the further pupil.

12. The system of claim 11, wherein the computing and control unit is configured to use the first eye intersecting line and a second eye intersecting line for determining expected co-ordinates of the center of the eyeball, the second eye intersecting line being different from the first eye intersecting line, the second eye intersecting line being determined for a second time as a line which is, in the direction of a second orientation vector of a second circle, parallel-shifted to a second center line by the expected distance, the orientation vector of a second circle and the second center line on which a center of the second circle is located being determined using the camera intrinsics and a second ellipse, so that a projection of the second circle, in a direction parallel to the second center line, onto the image plane is expected to reproduce a second ellipse at least substantially representing a border of the pupil at the second time in a second image of the eye of the user.

13. The system of claim 11, wherein the computing and control unit is configured to use a stored correction function taking into account corneal refraction to determine a corrected value for the parameter of the human eye, in particular for at least one of the center of the eyeball, the expected gaze direction of the eye, the expected optical axis of the eye, the expected orientation of the eye, the expected visual axis of the eye, the expected size of the pupil and the expected radius of the pupil.

14. The system of claim 11, wherein the expected distance between the center of the further eyeball and the center of the further pupil is at least substantially equal to the expected distance between the center of the eyeball and the center of the pupil, wherein the expected distance between the center of the eyeball and the center of the pupil is an average value, in particular a physiological constant, and/or wherein the further time is at least substantially equal to the first time.

15. The system of claim 11, wherein a position of the respective camera and/or an orientation of the respective camera is adjustable and/or fixable with respect to a frame of the head-wearable device.

16. The system of any claim 11, wherein the eye intersecting line is used for determining a parameter of the further eye.

17. The system of claim 11, wherein the computing and control unit is at least partly integrated into the head-wearable device and/or at least partly provided by a companion device of the system, in particular a mobile companion device.

* * * * *